(12) United States Patent
Park et al.

(10) Patent No.: US 9,089,351 B2
(45) Date of Patent: Jul. 28, 2015

(54) SHEATH FOR SURGICAL INSTRUMENT

(71) Applicant: INTUITIVE SURGICAL OPERATIONS, INC., Sunnyvale, CA (US)

(72) Inventors: William John Park, San Jose, CA (US); S. Christopher Anderson, San Francisco, CA (US); Thomas G. Cooper, Menlo Park, CA (US); Matthew R. Williams, Walnut Creek, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 21 days.

(21) Appl. No.: 13/739,583

(22) Filed: Jan. 11, 2013

(65) Prior Publication Data

US 2013/0123805 A1 May 16, 2013

Related U.S. Application Data

(63) Continuation-in-part of application No. 12/832,580, filed on Jul. 8, 2010.

(60) Provisional application No. 61/304,338, filed on Feb. 12, 2010.

(51) Int. Cl.
*A61B 19/00* (2006.01)
*A61B 18/14* (2006.01)
(Continued)

(52) U.S. Cl.
CPC ............ *A61B 19/20* (2013.01); *A61B 19/2203* (2013.01); *A61B 19/40* (2013.01); *A61B 18/1445* (2013.01); *A61B 2018/00083* (2013.01); *A61B 2019/082* (2013.01)

(58) Field of Classification Search
CPC ............... A61B 19/40; A61B 19/2203; A61B 19/2223; A61B 19/2242; A61B 2009/082; A61B 18/1445; A61B 18/1492; A61B 2018/0083; A61B 17/282; A61B 17/00234; A61B 2017/2929
USPC .............. 606/1, 121, 124, 125, 130, 186, 203
See application file for complete search history.

(56) References Cited

U.S. PATENT DOCUMENTS 5,261,918 A    11/1993   Phillips et al.
5,415,157 A     5/1995   Welcome
(Continued)

FOREIGN PATENT DOCUMENTS

EP    1738705 A1    1/2007
EP    2042117 A1    4/2009
(Continued)

OTHER PUBLICATIONS

Final Office Action mailed Jul. 5, 2013 for U.S. Appl. No. 12/832,580, filed Jul. 8, 2010.
(Continued)

*Primary Examiner* — Gary Jackson
*Assistant Examiner* — Boniface N. Nganga

(57) ABSTRACT

A surgical apparatus includes a shaft having a proximal end and a distal end, an end effector coupled to the distal end of the shaft, and a sheath disposed on an external surface of the instrument shaft. The sheath includes a material that is permeable to gas so as to permit equalization of a pressure differential after insertion of the sheath and shaft into an environment at a surgical insufflation gas pressure. The pressure differential is between an insufflation gas pressure and an initial pressure lower than the insufflation gas pressure.

23 Claims, 13 Drawing Sheets

(51) Int. Cl.
  *A61B 18/00* (2006.01)
  *A61B 19/08* (2006.01)

(56) References Cited

U.S. PATENT DOCUMENTS

| | | | |
|---|---|---|---|
| 5,417,203 A | 5/1995 | Tovey et al. | |
| 5,491,882 A * | 2/1996 | Walston et al. | 29/419.1 |
| 5,624,392 A | 4/1997 | Saab | |
| 5,724,994 A | 3/1998 | Simon et al. | |
| 6,004,509 A * | 12/1999 | Dey et al. | 422/28 |
| 6,016,848 A * | 1/2000 | Egres, Jr. | 138/137 |
| 6,091,993 A | 7/2000 | Bouchier et al. | |
| 6,106,540 A | 8/2000 | White et al. | |
| 6,817,974 B2 | 11/2004 | Cooper et al. | |
| 6,994,708 B2 | 2/2006 | Manzo | |
| 7,320,700 B2 | 1/2008 | Cooper et al. | |
| 7,367,973 B2 | 5/2008 | Manzo et al. | |
| 7,785,252 B2 | 8/2010 | Danitz et al. | |
| 7,879,035 B2 | 2/2011 | Garrison et al. | |
| 2002/0072712 A1 * | 6/2002 | Nool et al. | 604/167.01 |
| 2003/0125719 A1 | 7/2003 | Furnish | |
| 2003/0163128 A1 * | 8/2003 | Patil et al. | 606/41 |
| 2004/0098040 A1 | 5/2004 | Taniguchi et al. | |
| 2004/0122462 A1 | 6/2004 | Bakos et al. | |
| 2004/0230204 A1 | 11/2004 | Wortley et al. | |
| 2005/0216033 A1 | 9/2005 | Lee et al. | |
| 2006/0025654 A1 | 2/2006 | Suzuki et al. | |
| 2006/0079884 A1 | 4/2006 | Manzo et al. | |
| 2006/0079934 A1 | 4/2006 | Ogawa et al. | |
| 2006/0247743 A1 | 11/2006 | Hayakawa et al. | |
| 2007/0005001 A1 | 1/2007 | Rowe et al. | |
| 2007/0112337 A1 | 5/2007 | Salman et al. | |
| 2007/0179486 A1 | 8/2007 | Welch et al. | |
| 2007/0239203 A1 | 10/2007 | Cooper et al. | |
| 2008/0046122 A1 * | 2/2008 | Manzo et al. | 700/245 |
| 2008/0306335 A1 * | 12/2008 | Lau et al. | 600/106 |
| 2009/0082628 A1 | 3/2009 | Kucklick et al. | |
| 2009/0088738 A1 | 4/2009 | Guerra et al. | |
| 2009/0088741 A1 | 4/2009 | Hushka et al. | |
| 2009/0088747 A1 | 4/2009 | Hushka et al. | |
| 2009/0177141 A1 | 7/2009 | Kucklick | |
| 2009/0182201 A1 * | 7/2009 | Kucklick et al. | 600/156 |
| 2009/0254162 A1 * | 10/2009 | Quinci et al. | 607/115 |
| 2009/0287194 A1 | 11/2009 | Gertz et al. | |
| 2010/0016852 A1 | 1/2010 | Manzo et al. | |
| 2010/0168510 A1 * | 7/2010 | Rogers et al. | 600/104 |
| 2010/0268163 A1 | 10/2010 | Rowe et al. | |
| 2012/0010611 A1 | 1/2012 | Krom et al. | |
| 2012/0010628 A1 | 1/2012 | Cooper et al. | |
| 2012/0065472 A1 * | 3/2012 | Doyle et al. | 600/121 |
| 2012/0065645 A1 * | 3/2012 | Doyle et al. | 606/130 |
| 2014/0171943 A1 | 6/2014 | Weitzner et al. | |

FOREIGN PATENT DOCUMENTS

| | | |
|---|---|---|
| JP | 2010075565 A | 4/2010 |
| WO | 2005032642 A2 | 4/2005 |

OTHER PUBLICATIONS

Applicant Initiated Interview Summary mailed Oct. 23, 2013 for U.S. Appl. No. 12/832,580, filed Jul. 8, 2010.

Non-Final Office Action mailed Feb. 7, 2013 for U.S. Appl. No. 12/832,580, filed Jul. 8, 2010.

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

PCT/US2011/041842 International Search Report and Written Opinion of the International Searching Authority mailed Oct. 31, 2011, 10 pages.

* cited by examiner

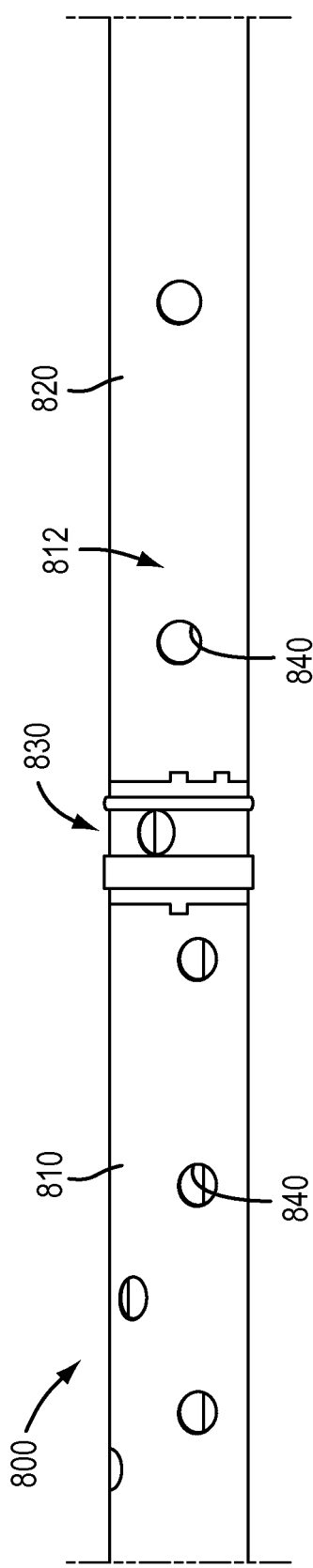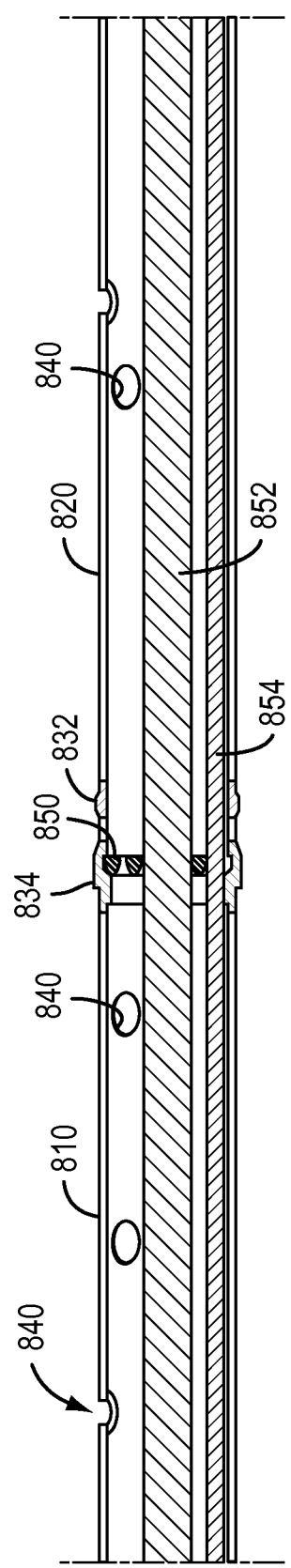

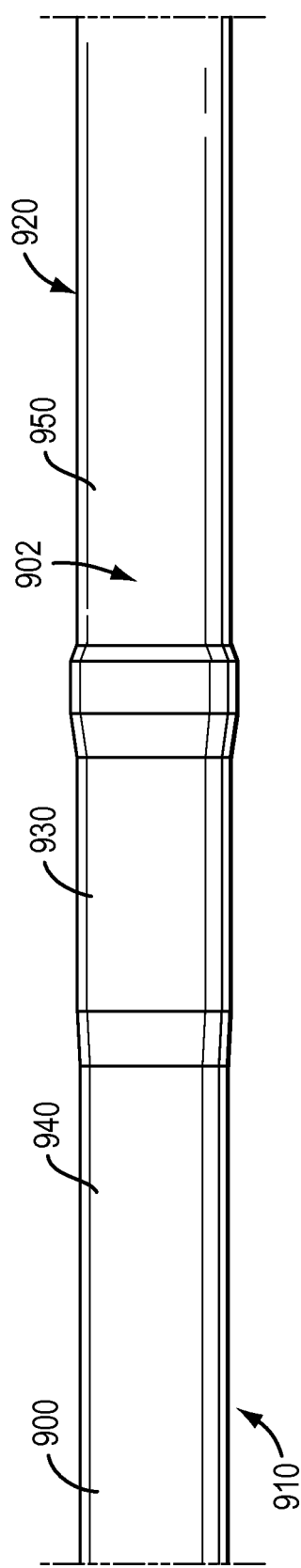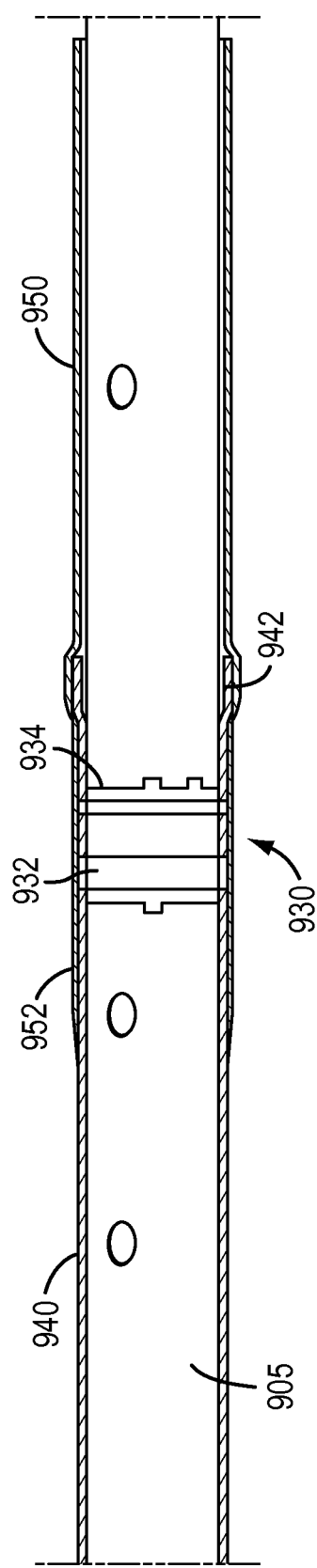
FIG. 9A
FIG. 9B

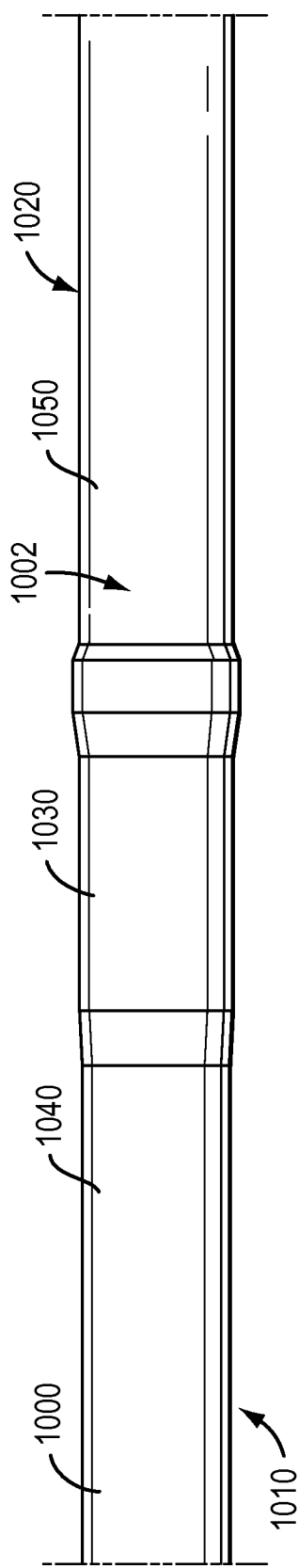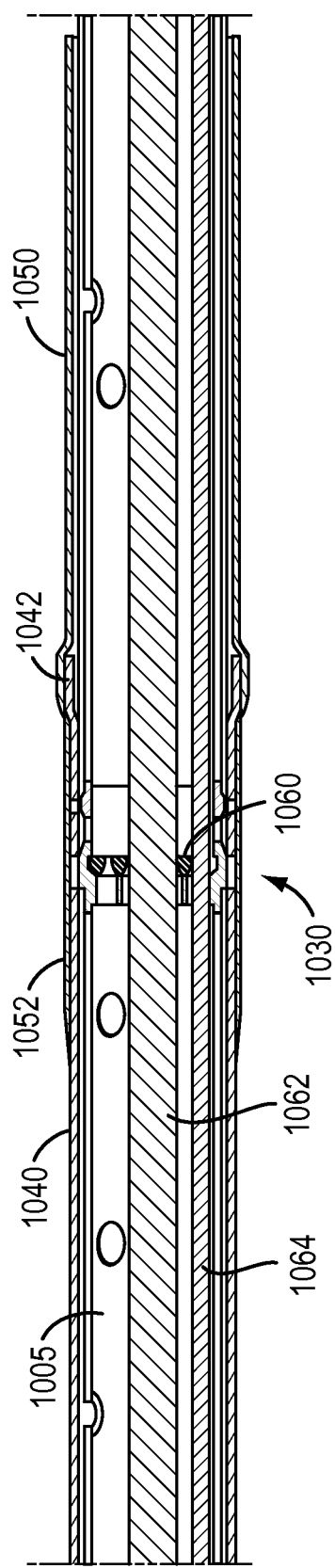

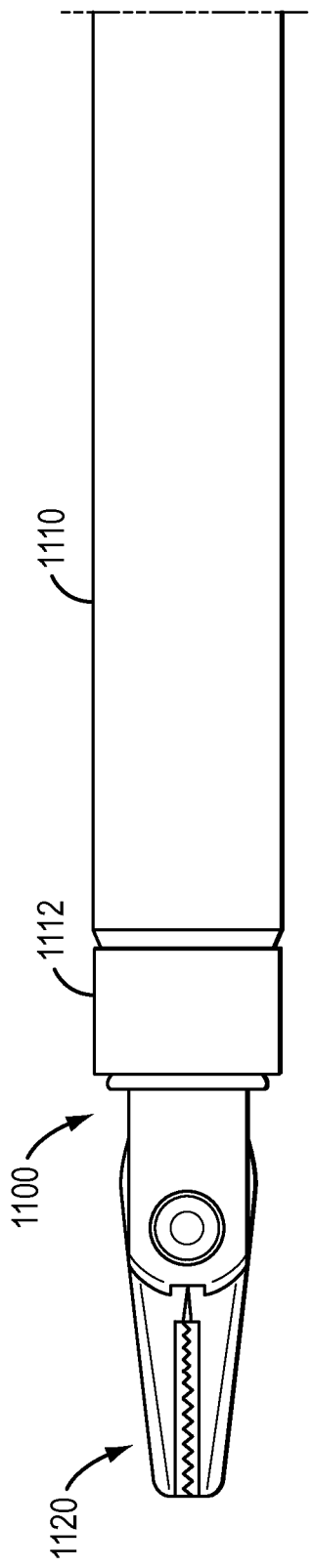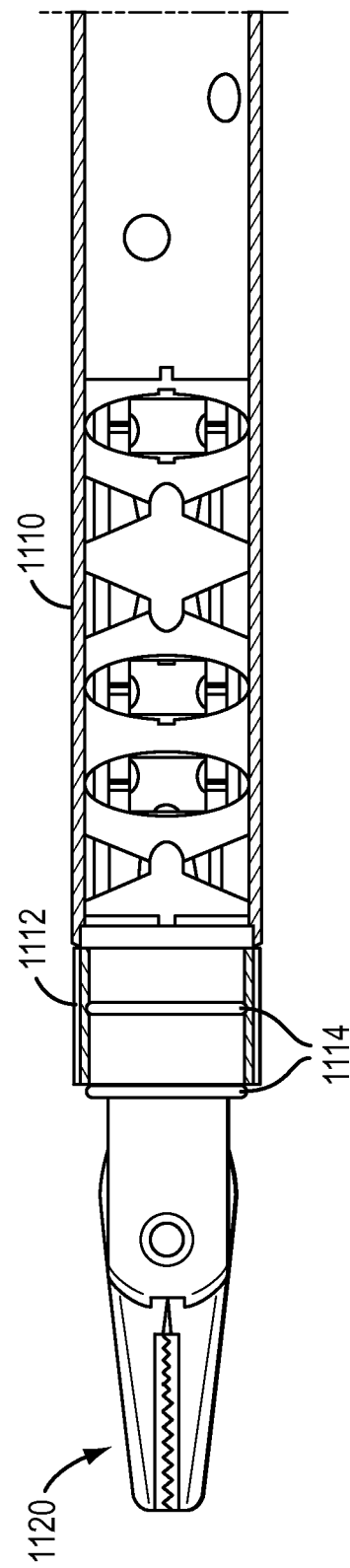

SHEATH FOR SURGICAL INSTRUMENT

CROSS-REFERENCE TO RELATED APPLICATIONS

This application is a continuation-in-part of U.S. patent application Ser. No. 12/832,580, filed Jul. 8, 2010, which claims benefit of the earlier filing date of U.S. Provisional Pat. App. No. 61/304,338, filed Feb. 12, 2010, each of which is hereby incorporated by reference in their entirety.

TECHNICAL FIELD

Aspects of the present disclosure relate to a sheath for a surgical instrument of a robotic surgical system. Other aspects related to a surgical instrument with a sheath for a robotic surgical system.

BACKGROUND

Robotically controlled surgical instruments are often used in minimally invasive medical procedures (as used herein, the terms "robot" or "robotically" and the like include teleoperation or telerobotic aspects). Such instruments typically include an end effector or tool such as forceps, a cutting tool, or a cauterizing tool mounted on a wrist mechanism at the distal end of an extension, sometimes referred to herein as the main tube of the instrument. During a medical procedure, the effector and the distal end of the main tube can be inserted directly or through a cannula into a small incision or a natural orifice of a patient to position the effector at a work site within the body of the patient. The wrist mechanism can then be used to position, orient, move, and operate the effector when performing the desired procedure at the work site. Tendons, e.g., cables or similar structures, extending through the main tube of the instrument can connect the wrist mechanism to a transmission or backend mechanism that may be motor driven in response to a doctor's instructions provided through a computer interface.

The instruments employed during medical procedures are generally complex mechanical devices having many separate components (e.g., cables and mechanical members). Accordingly, to reduce cost, it is desirable for the instruments to be reusable. However, reuse of a surgical instrument generally requires stringent cleaning and sterilization procedures that are made more difficult by the large number of small components and tight intervening spaces within such instruments. There exists a continued need for systems and methods that protect surgical instruments from exposure to fluids and debris during use, especially in more difficult to clean parts of the instrument. Systems and methods for improving the efficiency of cleaning procedures for minimally invasive surgical instruments and/or reducing the cost per use of such instruments are desired.

SUMMARY

Exemplary embodiments of the present disclosure may solve one or more of the above-mentioned problems and/or may demonstrate one or more of the above-mentioned desirable features. Other features and/or advantages may become apparent from the description that follows.

In accordance with at least one exemplary embodiment, a surgical apparatus includes a shaft having a proximal end and a distal end, an end effector coupled to the distal end of the shaft, and a sheath disposed on an external surface of the instrument shaft. The sheath comprises a material that is permeable to gas so as to permit equalization of a pressure differential after insertion of the sheath and shaft into an environment at a surgical insufflation gas pressure. The pressure differential is between an insufflation gas pressure and an initial pressure lower than the insufflation gas pressure.

In accordance with another exemplary embodiment, a surgical apparatus includes an instrument shaft having a proximal end and a distal end, an end effector coupled to the distal end of the shaft, and a sheath disposed on an external surface of the instrument shaft. The sheath has a first section made of ePTFE and a second section made of a second material. The second section provides a friction seal with the shaft.

In accordance with another exemplary embodiment a sheath for a surgical apparatus includes a tube configured to surround the surgical apparatus and provide a barrier to infiltration of liquids into the surgical apparatus. The tube comprises a material that is permeable to gas so as to permit an equalization of pressure between a pressure external to the sheath and a pressure internal to the sheath that is initially lower than the pressure external to the sheath.

In accordance with another exemplary embodiment, a method of using a sheathed surgical apparatus includes equalizing a pressure differential between a surgical insufflation gas pressure and an initial pressure lower than the insufflation gas pressure. The insufflation gas pressure is external to a portion of a surgical apparatus upon which a sheath is disposed and the initial pressure is within the surgical apparatus. Equalizing the pressure differential occurs via permeation of insufflation gas through the sheath.

Additional objects, features, and/or advantages will be set forth in part in the description which follows, and in part will be obvious from the description, or may be learned by practice of the present disclosure and/or claims. At least some of these objects and advantages may be realized and attained by the elements and combinations particularly pointed out in the appended claims.

It is to be understood that both the foregoing general description and the following detailed description are exemplary and explanatory only and are not restrictive of the claims; rather the claims should be entitled to their full breadth of scope, including equivalents.

BRIEF DESCRIPTION OF THE DRAWINGS

The present disclosure can be understood from the following detailed description, either alone or together with the accompanying drawings. The drawings are included to provide a further understanding of the present disclosure, and are incorporated in and constitute a part of this specification. The drawings illustrate one or more exemplary embodiments of the present teachings and together with the description serve to explain certain principles and operation.

FIG. 8A is a side view of an exemplary embodiment of a surgical instrument.

FIG. 8B is a side cross-sectional view of the surgical instrument of FIG. 8A.

FIG. 9A is a side view of another exemplary embodiment of a sheathed surgical instrument.

FIG. 9B is a side cross-sectional view of the sheathed surgical instrument of FIG. 9A.

FIG. 10A is a side view of another exemplary embodiment of a sheathed surgical instrument.

FIG. 10B is a side cross-sectional view of the sheathed surgical instrument of FIG. 10A.

FIG. 11A is a side view of yet another exemplary embodiment of a sheathed surgical instrument.

FIG. 11B is a side cross-sectional view of the sheathed surgical instrument of FIG. 11A.

DETAILED DESCRIPTION

Figure 1:
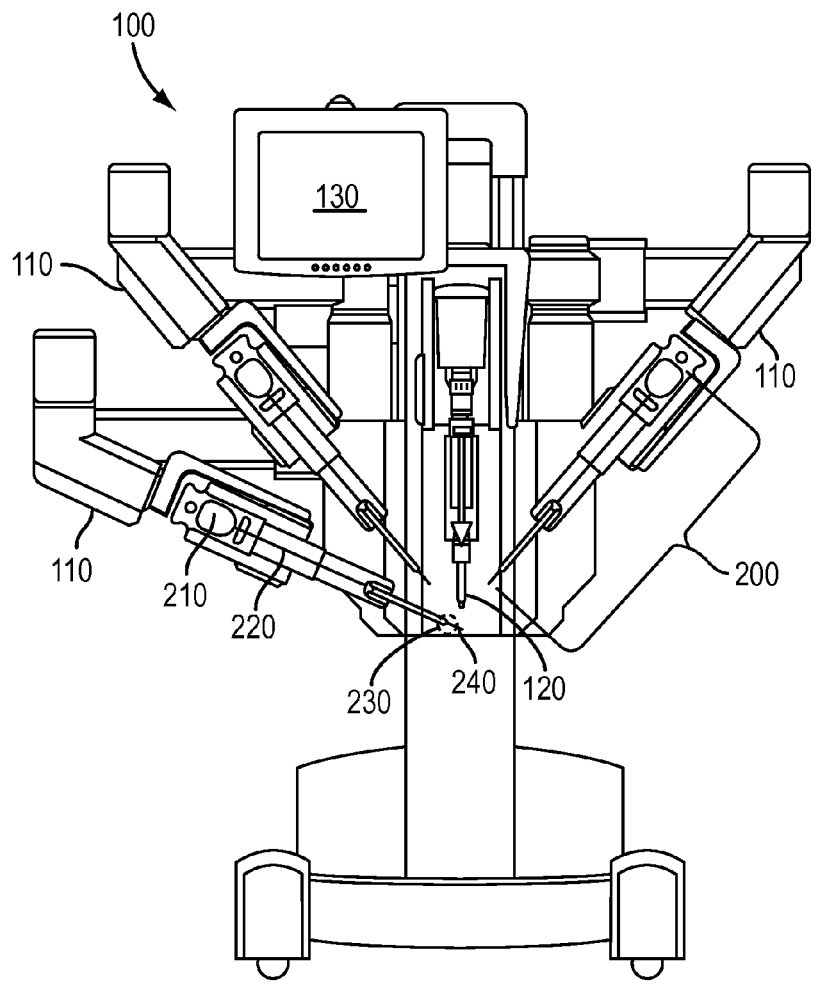
FIG. 1 shows a system having multiple arms on which instruments for minimally invasive medical procedures can be attached.

This description and the accompanying drawings that illustrate exemplary embodiments should not be taken as limiting. Various mechanical, compositional, structural, electrical, and operational changes may be made without departing from the scope of this description and the invention as claimed, including equivalents. In some instances, well-known structures and techniques have not been shown or described in detail so as not to obscure the disclosure. Like numbers in two or more figures represent the same or similar elements. Furthermore, elements and their associated features that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

For the purposes of this specification and appended claims, unless otherwise indicated, all numbers expressing quantities, percentages, or proportions, and other numerical values used in the specification and claims, are to be understood as being modified in all instances by the term "about," to the extent they are not already so modified. Accordingly, unless indicated to the contrary, the numerical parameters set forth in the following specification and attached claims are approximations that may vary depending upon the desired properties sought to be obtained. At the very least, and not as an attempt to limit the application of the doctrine of equivalents to the scope of the claims, each numerical parameter should at least be construed in light of the number of reported significant digits and by applying ordinary rounding techniques.

It is noted that, as used in this specification and the appended claims, the singular forms "a," "an," and "the," and any singular use of any word, include plural referents unless expressly and unequivocally limited to one referent. As used herein, the term "include" and its grammatical variants are intended to be non-limiting, such that recitation of items in a list is not to the exclusion of other like items that can be substituted or added to the listed items.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly.

In accordance with various exemplary embodiments, the present disclosure contemplates a surgical instrument for robotic minimally invasive procedures that employs a replaceable sheath to cover a wrist mechanism or other joints in the instrument. The instrument and the sheath can employ cooperative seal and retaining structures that keep the sheath in place on the instrument, seal the instrument from infiltration of biological material, and provide an opening for an end effector of the instrument to operate without obstruction. The replaceable sheath can provide a variety of functions including, for example, one or more of: reducing or preventing infiltration of biomaterial and/or other debris into the instrument during a medical procedure; providing electrical isolation of at least a portion of the surgical instrument; sealing the instrument to assist in maintaining an elevated pressure at the work site within a patient; providing smooth surface that facilitates insertion of the instrument through a cannula, reducing the chance that tissue will gather or pinch between openings in the joint mechanism, and reducing the chance that a wrist mechanism or other portion of one instrument will catch on or tangle another instrument or other components of a robotic medical system or other complex medical system.

Bending at a joint in a robotic surgical instrument typically causes a large difference between lengths of portions of a sheath at the inside and outside of the curve created at the joint, often resulting in strains on the order of 30 to 50% in a sheath. Many potential sheath materials that have desirable electrical characteristics are not sufficiently stretchy or flexible enough to withstand the strain at a bending joint. For example, materials such as polyester and fluoropolymers such as polytetrafluoroethylene (PTFE), ethylene tetrafluoroethylene (ETFE), fluorinated ethylene-propylene (FEP), and perfluoroalkoxy polymer resin (PFA) have relatively high dielectric strength but may not provide sufficient stretch or flexibility to withstand the bending at a mechanical joint. In accordance with various exemplary embodiments, such materials can be contoured (e.g., corrugated or convoluted) at locations corresponding to mechanical joints to accommodate length differences between the inside and outside of a bend. Alternatively, a sheath can be made of expanded or porous material (e.g., expanded PTFE or ePTFE) that provides a barrier to liquids and electrical current and also has a pore structure that allows the material to withstand the strain at a bend.

The material and construction of various exemplary embodiments of the sheaths described herein can be flexible at a wrist mechanism or other mechanical joints of the instrument so that a sheath by itself can provide a fluid or electrical barrier and the desired range of motion of the instrument without becoming caught in the covered components and mechanisms during instrument operation. Further, the sheath may also minimize or prevent gathering or pinching of tissue between openings in a joint mechanism. Accordingly, the sheaths can be used with jointed instruments without being damaged by instrument movement or interfering with the instrument operation.

In various exemplary embodiments, removable sheaths employed can contain or be internally coated with an agent such as a lubricant, a disinfectant, or an anticoagulant that lubricates mechanism of the instrument or facilitates cleaning of the instrument.

FIG. 1 shows an example of a robotically controlled system 100 that can employ sheathed instruments in accordance with an embodiment of the invention. System 100, which may, for example, be a da Vinci® Surgical System available from Intuitive Surgical, Inc., includes multiple surgical instruments 200, each of which is mounted in a docking port on a robotic arm 110. Instruments 200 can be interchangeable, so that the instruments 200 mounted on arms 110 can be selected for a particular medical procedure or changed during a medical procedure to provide the clinical functions needed. As is well known in the art, instruments 200 can implement many functions including but not limited to forceps or graspers, needle drivers, scalpels, scissors, cauterizing tools, and staplers.

The docking ports of system 100 generally include drive motors that provide mechanical power for operation of instruments 200. The docking ports may additionally include an electrical interface for communication with instruments 200, for example, to identify the type of instrument in the docking port, to access parameters of the instrument, or convey measurements obtained using the instruments. High voltage electrical systems (not shown) such as generators for cauterizing or sealing instruments would typically connect to suitable instruments 200 through separate connectors but could alternatively be provided through built-in circuits in control system 100.

Each instrument 200 generally includes a transmission or backend mechanism 210, a main shaft 220 extending from the backend mechanism 210, an optional wrist mechanism 230 at the distal end of main shaft 220, and an end effector 240 extending from wrist mechanism 230 or directly from the shaft 220. Drive cables or tendons and electrical conductors that are connected to wrist mechanism 230 in an instrument 200 may extend through main shaft 220 and connect to backend mechanism 210. Backend mechanism 210 typically provides a mechanical coupling of the drive tendons to drive motors in control system 100. System 100 can thus control movement and tension in the tendons as needed to move or position wrist mechanism 230 and operate end effector 240. A camera system 120 can similarly be mounted on an arm of system 100 and have a wrist mechanism that system 100 operates to position a distal end of camera system 120 for viewing of a work site and the operation of instruments 200 within a patient. The views from camera system 120, which may be stereoscopic or three-dimensional, can be viewed at a control console (not shown) and images may be displayed on a monitor 130. A processing system of system 100 can thus provide a user interface enabling a doctor or other medical personnel to see and manipulate the camera system 120 and instruments 200. For example, an arm 110 can be used to insert the end of a surgical instrument 200 through a cannula in small incisions in a patient undergoing a medical procedure and to operate wrist mechanism 230 and end effector 240 at a worksite inside the patient. The diameter or diameters of main shaft 220, wrist mechanism 230, and end effector 240 are generally selected according to the size of the cannula with which the instrument will be used, and in an exemplary embodiment, wrist mechanism 200 and main shaft 220 are about 4 mm, 5 mm, or 8 mm in diameter to match the sizes of some existing cannula systems.

Main shaft 220 may contain both drive tendons and electrical conductors that run from backend mechanism 210 to wrist mechanism 230 and end effector 240. In general, main shaft 220 may be rigid or flexible. A flexible main shaft 220 would be used, for example, for insertion through an endoscope or other guide or cannula that follows a natural lumen or otherwise curved path. However, many common types of minimally invasive medical procedures such as laparoscopic surgery employ straight cannulas for insertion and removal of instruments, which may permit use of a rigid main shaft 220. A rigid main shaft 220 can provide a more solid base for use of wrist mechanism 230 and end effector 240 during a medical procedure. A rigid and straight main shaft 220 also permits portions of drive tendons extending through main tube 110 to be structures such as rods or tubes (e.g., hypotubes) that may provide better immunity to stretching or be less expensive. Whether flexible or rigid, main shaft 220 would generally experience minimal movement during operation of wrist mechanism 230.

Figure 2:
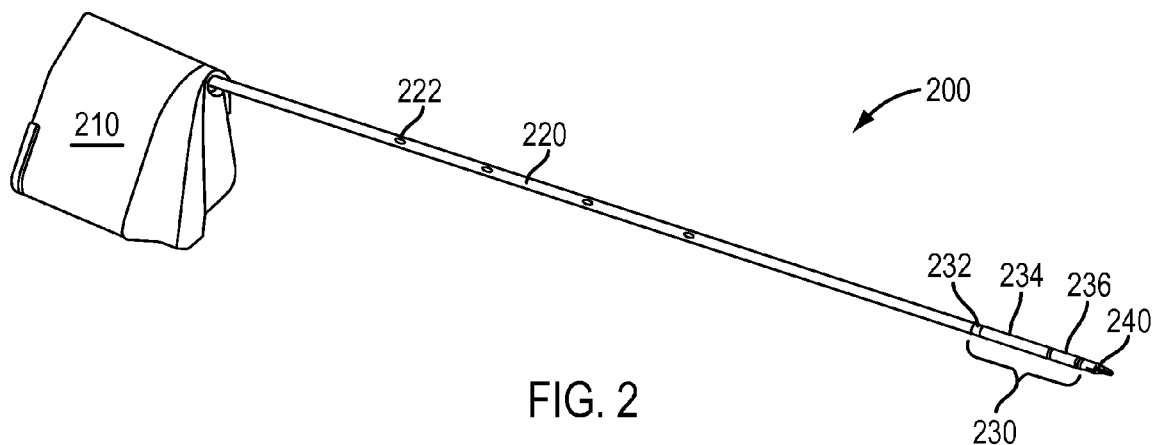
FIG. 2 shows an instrument that may be employed in the system of FIG. 1 and use replaceable sheaths in accordance with an exemplary embodiment.

FIG. 2 diagrammatically shows an exemplary surgical instrument 200 in more detail and particularly illustrates one specific embodiment of a wrist mechanism 230 and end effector 240, which are the components of surgical instrument 200 that generally move extensively during a medical procedure. In the illustrated embodiment, wrist mechanism 230 includes a joint 232 that connects an extended member 234 to main shaft 220, and extended member 234 connects to a multi-member wrist 236 on which end effector 240 is mounted. Joint 232 can have two angular degrees of freedom for movement of member 234, which, as a result of the extended length of member 234, provides a significant range of spatial motion for wrist 236 and end effector 240. Wrist 236 includes multiple vertebrae that may be independently controlled to provide multiple degrees of freedom for moving and orienting end effector 240 during a medical procedure. The specifics of wrist mechanism 230 are provided here as merely as an illustration of one type of wrist mechanism. Many other types of wrist mechanisms are known and could be used with removable sheaths as described herein. For example, U.S. Pat. No. 6,817,974, entitled "Surgical tool having Positively Positionable Tendon-Actuated Multi-Disk Wrist Joint," to Cooper et al., which is hereby incorporated by reference herein in its entirety, describes various wrist mechanisms containing multiple disks and tendon controlled joints. In some cases, wrist mechanisms in surgical instruments have joints with significant ranges of articulation (e.g., up to 30 degrees or 40 degrees from straight for a single joint), and each joint may be repeatedly exercised during typical medical procedures. Such joints pose challenges for sheathing the instruments because overly compliant sheathing can interfere with joint motion, be pinched during joint motion, and/or wear through as the result of repeated motion. On the other hand, sheathing that is too stiff may restrict joint motion and/or tear.

FIG. 2 also illustrates that main shaft 220 may include one or more cleaning holes 222, which facilitate cleaning of the interior of instrument 200. Conventionally, such cleaning holes have the drawback of creating flow paths for biological material or gas flow from a region of elevated pressure that may be maintained in a patient during a medical procedure. For instance, insufflation may be practiced, which involves distending at least a portion of a body cavity with a positive pressure of insufflation fluid, such as a clear fluid or gas. For example, an insufflation fluid may be carbon dioxide.

In accordance with an exemplary embodiment, a replaceable sheath can be installed on instrument 200 and seal cleaning holes 222 to help maintain a pressure differential during a medical procedure. Further, the sheath can be removed, for example, between medical procedures, to permit access to cleaning holes 220 when instrument 200 is cleaned. Cleaning holes (not shown) can also be included in wrist mechanism 230, for example, in extended member 234. The sheath can also seal wrist mechanism 230 but in case of contamination, can be removed to permit cleaning of an instrument protected by the sheath. On a camera instrument, which may be relatively large or have lower mechanical load requirements, the cleaning holes can be made large to enable easy cleaning, while the sheath reduces the amount of access that biomaterial has to the camera system during use. Instruments such as camera systems that are not generally in direct contact with biomaterial may not require a full seal.

Figure 3A:
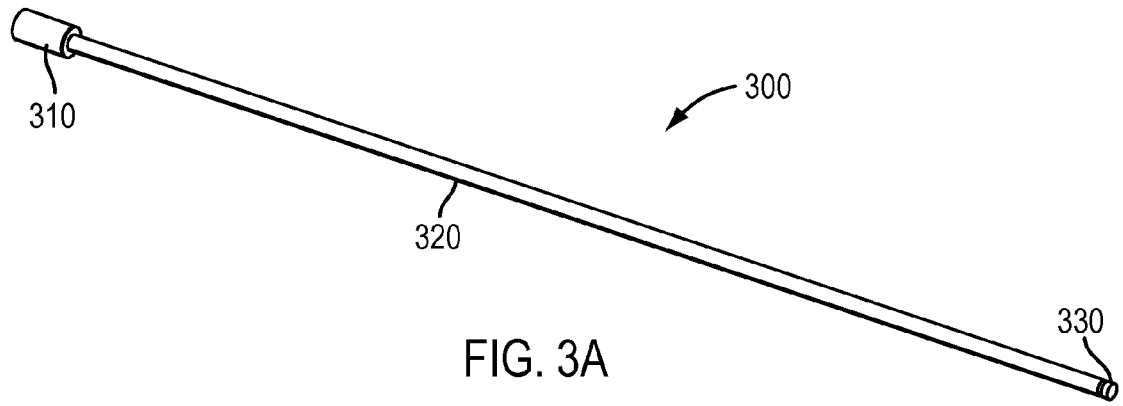
FIG. 3A shows a sheath in accordance with an exemplary embodiment having flexible pressure fit end seals.

FIG. 3A shows a sheath 300 in accordance with one exemplary embodiment of the invention that can be used with a jointed surgical instrument. Surgical instrument is used here in a broad sense to include both surgical instruments 200 with end effectors and camera systems 120 such as described above with reference to FIGS. 1 and 2 and any similar components of a medical apparatus that may be employed in a minimally invasive medical procedure. Sheath 300 includes a first end piece or base 310, a tube or generally tubular body 320, and a second end piece or tip 330. Sheath 300 has an inner diameter sized to accommodate the main shaft (e.g., shaft 220) of a surgical instrument (e.g., typically ranging from 4 mm to 8 mm), and tube 310 and tip 330 may have an outer diameter sized to fit within a cannula, which may be employed to guide the instrument.

Body 320 generally provides a flexible abrasion resistant surface that can act as a barrier to fluids and/or electricity. In an exemplary embodiment, body 320 is made of a relatively rigid material that resists kinking, buckling, or cracking. For example, body 320 may be a tube of a polyester such as Mylar, for example a fluoropolymer such as, for example, PTFE, ETFE, FEP, and PFA; a polyimide such as Kapton, for example, a thermoplastic elastomer, such as polyether block amide (PEBA) (e.g., Pebax®, such as Pebax® 7233), for example, or a multi-ply construction including different materials such as, for example, Mylar, Kapton, urethane, silicon or a woven fiber such as a para-aramid synthetic fiber (e.g., Kevlar®) Tube 320 would typically have a circular cross-section but may have any cross-section as desired to match a surgical instrument or camera system being sheathed. A typical sheath may have one or more layers with an exemplary wall thickness of about 0.003" depending on requirements for the strength, flexibility, and electrical insulating properties of the sheath. In another example, a sheath may have one or more layers with an exemplary wall thickness of about 0.010". In one exemplary embodiment, tube 320 can employ heat shrinkable polyester tubing, which is commercially available from suppliers such as Advanced Polymers, Inc. However, with a multi-ply construction, the different materials can be chosen to add different overall characteristics to the sheath. For example, Kapton and Mylar would provide good dielectric properties while a para-aramid fiber would provide structural stability. As described further below, a high degree of elasticity or accommodation of bending may not be required for most of body 320, so that the composition of the portions of body 320 that do not bend can be selected for other desirable characteristics such as, for example, a high dielectric constant when electrical isolation is desired or lower processing temperature to support higher volume, lower cost sheath manufacturing.

End pieces 310 and 330 seal against a surgical instrument as described further below. End pieces 310 and 330 may be predominantly made of a flexible material, such as, for example, silicone or urethane, which is molded over and/or bonded to opposite ends of body 320. End piece 310 or 330 may further include a more resilient portion that is shaped to removeably lock into a complementary feature on a surgical instrument to keep sheath 300 in an installed position until sheath 300 is removed for instrument cleaning.

Figure 3B:
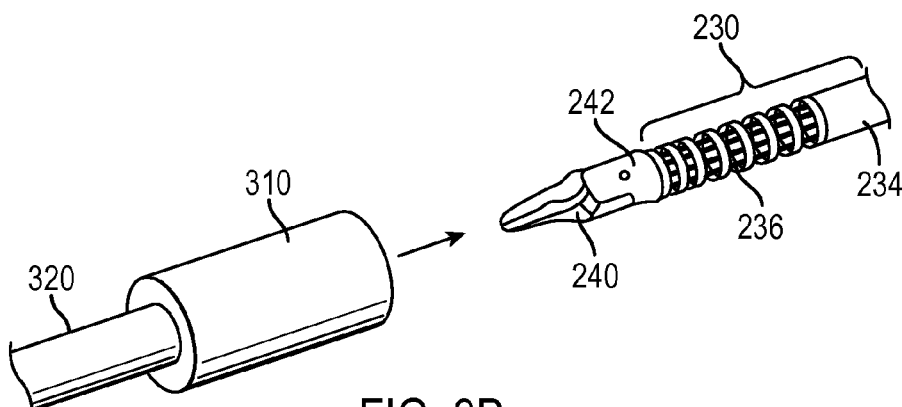
FIG. 3B illustrates installation of the sheath of FIG. 3A onto the instrument of FIG. 2.

Sheath 300 can be installed on an instrument 200 by sliding sheath 300 over the end effector 240, wrist mechanism 230, and main shaft 220 as illustrated in FIG. 3B. In an exemplary embodiment, a large section of sheath body 320 is relatively rigid and holds its shape during and after installation. For example, the material or composition of one section of body 320 is sufficiently rigid to avoid buckling during installation or as a result of friction with a cannula during medical procedures when a cannula guides an instrument having a sheath 300 installed.

Figure 3C:
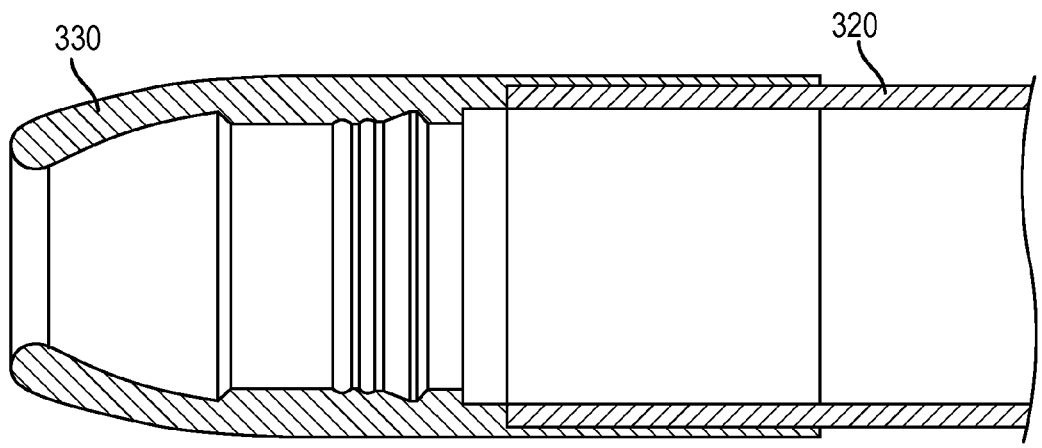
FIG. 3C illustrates a portion of a sheath in accordance with an exemplary embodiment having an end piece with an interior shaped to fit against the mechanism of a surgical instrument.
Figure 3D:
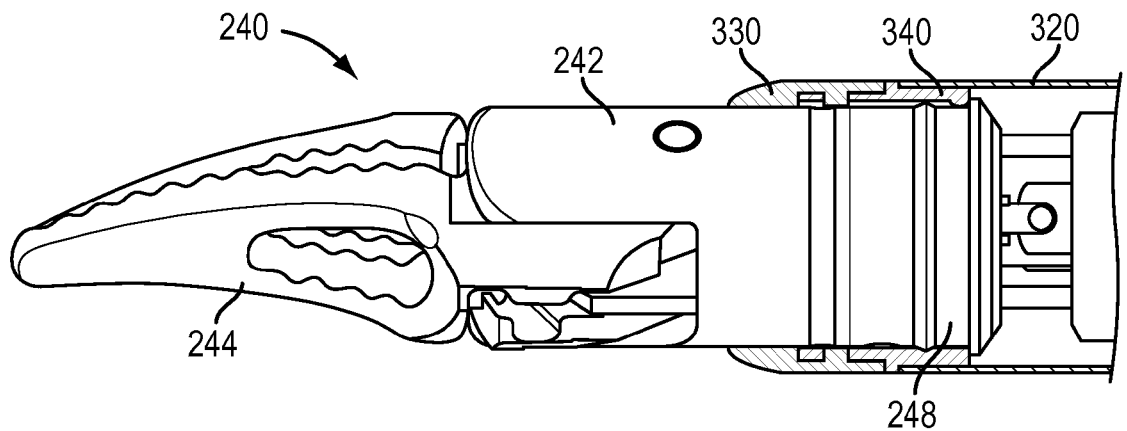
FIG. 3D is a partial cutaway view showing details of a distal seal and retaining structure in accordance with an exemplary embodiment.

End pieces 310 and 330, which may be bonded to body 320, contain an elastic material and stretch over the instrument during installation of sheath 300. The elastic material in ends 310 and 320 can provide friction seals against respective surfaces of effector 230 and main shaft 220. FIG. 3C, for example, illustrates an embodiment of sheath 300 in which tip 330 has an interior profile shaped to match the outer surface of the portion of the surgical instrument (e.g., a portion of the end effector 240), so that tip 330 tends to fit into and remain in a desired position on the instrument. As shown in FIG. 3D, elastic tension in tip 330 can cause tip 330 to seal against a base member 242 (e.g., clevis) of end effector 240. End effector 240, as shown, extends through an opening in tip 330 so that working portions (e.g., scissors or forceps jaws 244) of end effector 240 are unobstructed when sheath 300 is installed. Optionally, separate seals (not shown) can be provided for tendons or other structures that may extend through base member 342 for operation of end effector 240.

FIG. 3D also illustrates that sheath 300 may additionally include a retaining structure 340 such as a snap-fit mechanism. For example, retaining structure 340 can be made of a resilient material such as a plastic (e.g., ultem) that flexes away from instrument 200 during installation of sheath 300 and snaps into a complementary groove 248 in base member 242 when sheath 300 reaches a fully installed position. Alternatively, retaining structure 340 could include a female thread pattern that engages a complement thread pattern on base member 242 or elsewhere on instrument 200. Retaining structure 340, when engaged with instrument 200, resists further movement of sheath 300 during installation and use of instrument 200, while being easily removed by hand or with a suitable removal tool.

Figure 3E:
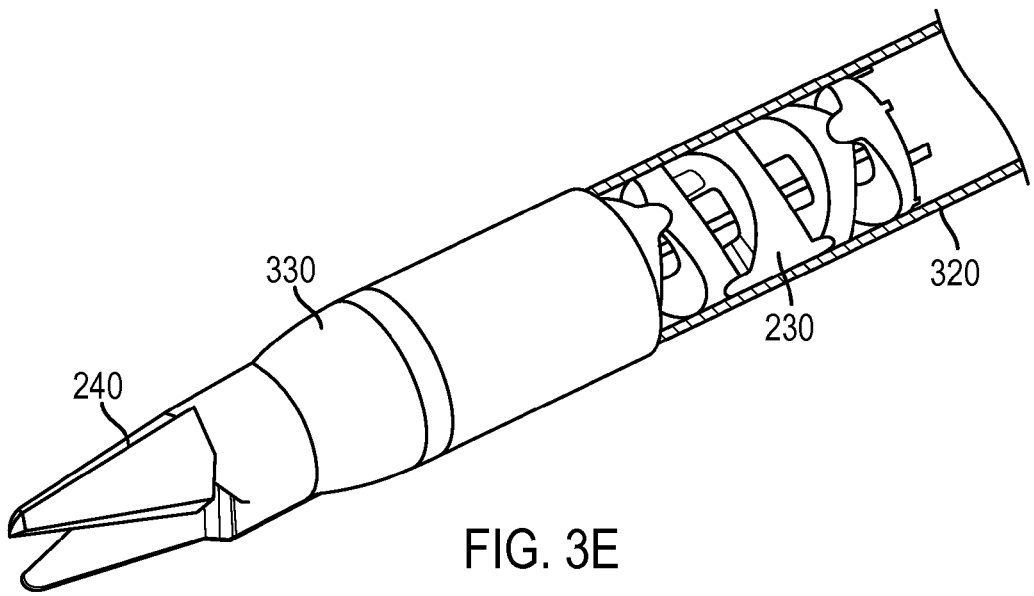
FIG. 3E shows a partial cutaway view of the distal end of an instrument with a removable sheath installed in accordance with an exemplary embodiment.

FIG. 3E shows tip 330 in the fully installed position with an end effector 220 extending outward from the distal opening of tip 330. However, joints of wrist mechanism 230 are surrounded by a section of body 320 that provides the flexibility to accommodate bending of wrist mechanism 230 without being damaged or interfering with the movement of joints. As described further below, this may be achieved in that section of body 320 by providing convolutions in body 320, employing a material with suitable pore structure, or employing a flexible material with an integrated support structure.

Figure 3F:
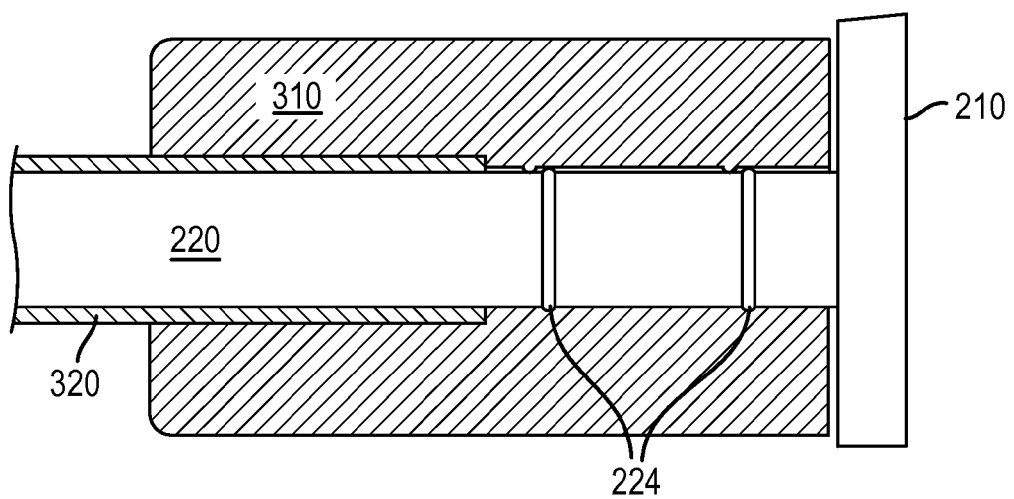
FIG. 3F is a partial cutaway view showing details of a proximal end of an instrument with a removable sheath installed in accordance with an exemplary embodiment.

End piece or base 310 similarly seals sheath 300 when installed on an instrument. In one embodiment of the invention, base 310 is positioned at or near backend mechanism 210 of instrument 200 when sheath 300 is fully installed. FIG. 3F, for example, illustrates a configuration where base 310 is adjacent to backend mechanism 210 and provides a friction seal against main shaft 220. With this configuration, sheath 300 can seal and or electrically isolate nearly the entire length of main shaft 220. FIG. 3F also illustrates that main shaft 220 may optionally have ridges 224 or other features shaped to engage base 310 to provide a more secure seal or better retain, e.g., resist slipping of, sheath 300 during a medical procedure. Base 310 may further include a retaining structure (not shown) made of a resilient material that engages a complementary feature of main shaft 220 to releaseably lock the proximal end of sheath 300 in place.

Figure 4A:
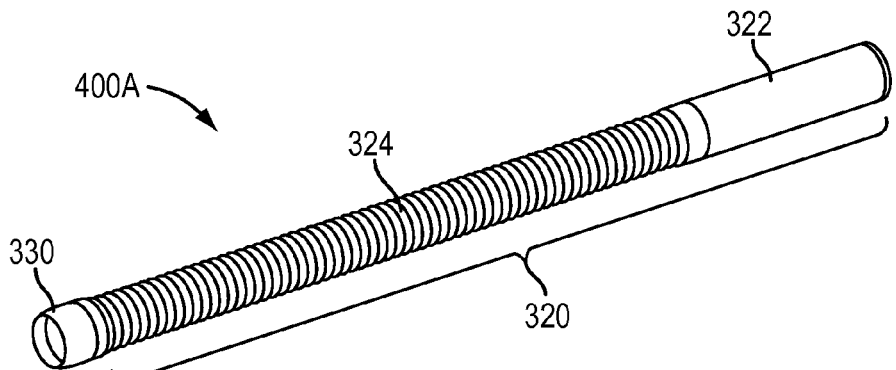
FIG. 4A illustrates a portion of a sheath in accordance with an exemplary embodiment using corrugations to improve flexibility where the sheath covers a wrist mechanism.

Sheath 300, as described above, can cover a wrist mechanism 230 when installed on a surgical instrument 200. In accordance with an exemplary embodiment, the section of body 320 that is positioned to surround wrist mechanism 230 (or other joints in a surgical instrument) is fabricated to provide the necessary flexibility for movement of the wrist mechanism without being caught in the wrist mechanism or otherwise becoming damaged or interfering with movement of the surgical instrument. Further, the force required to bend sheath 300 at the joints should also be small, so that sheath 300 does not interfere with the range of motion of the instrument or the therapeutic forces that the instrument can deliver when used in a robotic medical apparatus. FIG. 4A illustrates an exemplary embodiment of the invention in which body 320 includes two tubular sections 322 and 324 that can be made of the same basic material or composition but are shaped to create different flexibilities. In particular, section 324 is corrugated or convoluted in a manner that allows section 324 to bend without kinking or collapsing and allows section 324 to be repeatedly bent without creating stress fractures or fatigue fractures.

Convolutions in section 324 can be made, for example, by heat shrinking a material such as polyester that is wrapped around a spring held at fixed length while the polyester is also held at a fixed length. The first heating will thus form convolutions with a spacing defined by coils of the spring. The material can then be further shrunk with the spring free to contract, or even with the spring under axial compression, to increase the depth of the convolutions and increase flexibility. The spring used in the fabrication of section 324 can be left in sheath 300 as a support structure or removed.

The required length and position of section 324 in general will depend on the location of the joints in the instrument to be sheathed. In the example of FIG. 4A, section 324 is at the distal end of sheath 300, which corresponds to the locations of wrist mechanism 230 including multi-member or snake joint 232, extended member 234, and joint 236 in instrument 200 (FIG. 2). If additional mechanical joints were present along the instrument to be sheathed, the length of section 324 could be extended to cover other joints, or body 320 could include multiple separated, corrugated or convoluted sections for the separated mechanical joints. Covering joints in this manner can be advantageous when an instrument is inserted through a cannula because sheath 320 can prevent mechanical links within the joints from snagging on features of the cannula such as a trapdoor or seals. Section 322 of body 320 is preferably more rigid than section 324 to better resist buckling and provide a smoother structure for installation on an instrument, insertion through a cannula, and sealing on a cannula seal. The greater rigidity of section 322 can be inherent to the straight rather than convoluted topography of section 322, or section 322 may additionally be made thicker than section 324, have thicker layers than does section 324, or have a different composition from section 322. In general, the maximum permitted outer diameters of both sections 322 and 324 are limited by the cannula used with an instrument on which sheath 300 is installed, so that the lack of convolutions in section 322 permits use of thicker material in section 322.

Sheath 300 can employ other or additional techniques or structures to alter the stiffness of different sections of body 320. For example, body 320 can include multiple layers of different materials such as a Mylar layer surrounded by structural fiber (e.g., a woven or braided aramid fiber) and then another layer of Mylar. Walls in one or more sections of body 320 could then have different thicknesses for one or more of the layers to modify the relative stiffness of a section (e.g., section 324) that surrounds an instrument joint when compared to a section (e.g., section 324) of body 320 that surrounds a rigid member or portion of the main tube of the instrument. For example, section 322 could have an outer layer of Mylar about 0.006" thick, a layer of fiber about 0.003" thick, and an inner layer of Mylar about 0.003 to make a stiff tube, while section 324 has an outer layer of Mylar about 0.002" thick, reinforcing fiber about 0.003" thick, and the inner layer of Mylar about 0.002" thick. The different sections could also be formed over a spring or corrugated mandrel that form convolutions in section 324 to assist with the flexibility of the multilayer sheath.

In accordance with yet another exemplary embodiment of the invention, a one-piece sheath made of a stretchy material, such as, for example, silicone or urethane, which has a tendency to collapse when a joint bends, can be re-enforced with an integrated spring or other structure that allows the material to better retain its cross-sectional shape or diameter when bent. For example, a sheath made of silicone tube can contain a coil spring extending either along the length of body 320 or the section 324 of sheath 300 that is intended to cover one or more joints of an instrument. Use of a flexible or stretch material allows integration of end pieces 310 and 330 in a single molded structure with body 320.

Figure 4B:
FIG. 4B illustrates a portion of a sheath in accordance with an exemplary embodiment in which the material in a section of a sheath covering a wrist mechanism differs from the material in an adjacent portion of the sheath.

FIG. 4B shows an exploded view of an alternative embodiment in which body 320 has separate pieces corresponding to sections 322 and 324B each made of different materials. For example, section 322 and a retaining structure 340 can be made of a relatively rigid material such as polyester, a multi-ply Mylar/Kapton or a rigid silicon or urethane, while section 324B is made of a more flexible material such as a more flexible silicone or urethane. The flexibility of the material in section 324B permits molding tip seal 330 as an integral part of section 324B. However, such flexible materials may be too soft and prone to kinking, so that all or a portion of section 324B can be reinforced, for example, with braided fiber or a coil spring that could be on the inside diameter, outside diameter, or within the material of section 324. The tubular sections 322 and 324B of different materials or different durometer of the same material are bonded or glued together to form body 320. FIG. 4B also illustrates that retaining structure 340, which is preferably made of a more rigid material, can be bonded to section 324B, so as to extend through a cutout in section 324B, enabling structure 340 to engage a complementary feature of an instrument to be sheathed, thereby locking sheath 400C in a desired location.

Figure 4C:
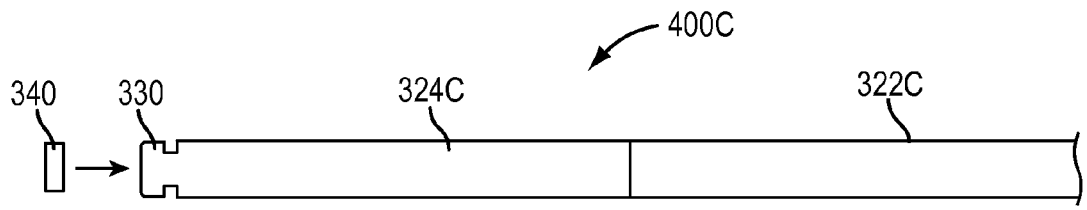
FIG. 4C illustrates a portion of a sheath in accordance with an exemplary embodiment that processes sections of the sheath differently to create different flexibility characteristics in different sections of the sheath.

FIG. 4C shows a portion 400C of yet another embodiment of a sheath having sections 322C and 324C made of the same initial material but may be processed to provide different characteristics. In particular, both sections 322C and 324C sheath 400C can made of a material such as silicon or expanded PTFE (ePTFE). However, section 322C may be processed or chemically treated to increase rigidity and improve abrasion resistance or section 324C may be treated or processed to improve performance during bending. The processing or treatment of a section may, for example, be a coating or dye that stiffens section 322C to facilitate installation of sheath 400C.

In an exemplary embodiment of sheath 400C, body 320 is made of PTFE that is processed at least in section 324C to make the PTFE porous, i.e. expanded PTFE or ePTFE. The density of PTFE in section 324C can thus be manipulated to provide the desired characteristics. For example, PTFE can be extruded and then stretched on an annealing mandrel to give the PTFE small tears or pores. The degree of porosity and the thickness of the PTFE material in section 324C can be selected to provide the required flexibility characteristics when the joint surrounded by section 324B bends. In particular, at a bending joint, one side of section 324B stretches or gets longer, while the other side contracts or gets shorter. The pores in section 324B open and close as the joint bends, so that section 324 can avoid changing in diameter and therefore does not get trapped or pinched by the bending joint. ePTFE capable of bending in this manner is available commercially, for example, from International Polymer Engineering of Tempe, Ariz. Section 324 when made of ePTFE can have a silicone tip molded onto its ends to provide seals as described above or the ePTFE can provide a tension or friction seal when the ePTFE conforms to the underlying surface of the instrument. One advantage of PTFE is that it is very slick, which facilitates installation on an instrument and insertion of a sheathed instrument through a cannula. Colorant can be added to the PTFE or other material of the sheath, for example, to provide a less bright color, such as gray, if the bright white color of PTFE or other material is distracting or causes saturation of the contrast of a camera system in a robotic medical system.

A sheath may be used with a surgical instrument, such as a surgical instrument of a robotic surgical system, to minimize or prevent biomaterials from being introduced into the body of the instrument, such as into difficult to clean areas of the instrument, as discussed above. Thus, a sheath may be used to cover portions of the instrument. However, one consideration when using a sheath with a surgical instrument is whether the sheath could become compromised, which could lead to the introduction of biomaterial, such as blood, within the instrument.

Figure 6:
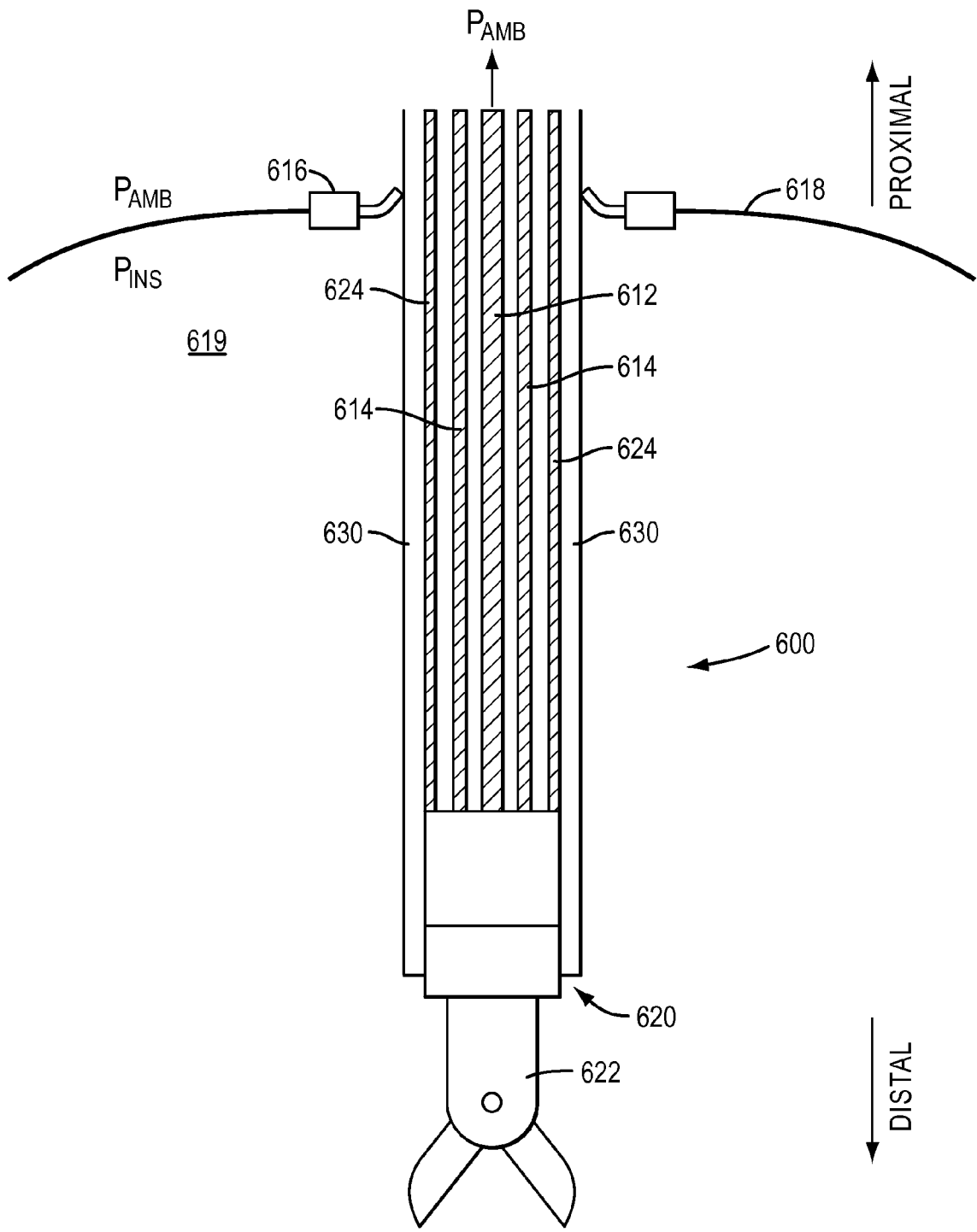
FIG. 6 is a cross-sectional view of an exemplary embodiment of a sheathed surgical instrument inserted into a body cavity.

Turning to FIG. 6, an exemplary embodiment of a distal portion of a sheathed surgical instrument 600 is shown inserted through a body wall 618 and into a cavity 619 of a body. The sheathed surgical instrument 600 may include, for example, a sheath 630 and a surgical instrument having a main shaft 624 with a proximal end (not shown) and a distal end 620. The proximal and distal directions relative to the instrument are labeled as such in FIG. 6. An end effector 622 may be located at the distal end 620 of the main shaft 624 and one or more force transmission devices may extend from an actuator or other force transmission device (not shown) at the proximal end to the distal end 620 of the instrument. For instance, a rod or cable 612 may be provided to actuate the end effector 622. One or more conduits or cables 614 may be provided to provide electrical power, a fluid conduit, or another type of pathway along the instrument. As will be discussed below and as mentioned above with reference to FIG. 2, the shaft 624 of the instrument may include one or more cleaning holes (not shown), such as to assist with cleaning the instrument. The sheath 630 may be provided to cover the body 624, including the holes in the body 624, to assist with preventing introduction of biomaterial within the body 624 of the instrument or even onto an outer surface of the body 624 of the instrument.

As mentioned above, during a surgical procedure, insufflation pressure $P_{INS}$ may be introduced within a patient's body cavity. The insufflation pressure $P_{INS}$ may be a positive pressure greater than an ambient pressure $P_{AMB}$ of the general environment surrounding the patient's body, such as in an operating room. As a result, the insufflation pressure $P_{INS}$ may expand the volume of the internal body cavity of a patient and provide more space for a surgical procedure to operate within. Further, the expanded space within the body cavity may also facilitate viewing of the surgical instruments during the procedure.

As discussed above, a sheath may advantageously serve as a barrier to separate different atmospheric pressures from one another. As shown in the example of FIG. 6, a sheathed surgical instrument 600 may be inserted through a wall 618 of a patient and into the body cavity 619. A port 616 placed in the body wall 618 so that the port 616 seals against the sheathed surgical instrument 600 is shown in FIG. 6. The proximal end and other portions of the sheathed surgical instrument 600 that are not in the cavity 619 may be exposed to the ambient pressure $P_{AMB}$ surround the patient's body, such as via actuators or other devices attached to the proximal end of the sheathed surgical instrument 600 located external to patient's body that are not sealed against the ambient pressure $P_{AMB}$ of the surrounding environment. Depending on its configuration and sealing to the instrument shaft and body wall of a patient, sheath 630 located on the body 624 of the instrument may serve as a barrier to not only minimize or prevent introduction of biomaterial within the instrument, but also as a barrier separating the relatively high insufflation pressure $P_{INS}$ surrounding the instrument within the body cavity 619 from the lower ambient pressure $P_{AMB}$ within the instrument.

In such a configuration, however, if the sheath 630 were to become compromised, the pressure gradient across the sheath 630 between the relatively high insufflation pressure $P_{INS}$ and the lower ambient pressure $P_{AMB}$ may cause introduction of biomaterial into the surgical instrument. For instance, as shown in FIG. 6, a puncture or hole could develop in the sheath 630, permitting the interior of the instrument to be exposed to the environment of the body cavity 619. If the body cavity is at an insufflation pressure $P_{INS}$ that is higher than the ambient pressure $P_{AMB}$ within the instrument, material from within the body cavity 619 may be forced through the puncture or hole in the sheath 630 to within the interior of the surgical instrument. As a result, biomaterial within the body cavity 619 may be forced or drawn into the surgical instrument, soiling or contaminating the instrument in a way that is difficult or time consuming to clean. This phenomena may be referred to as a "straw effect."

Figure 7:
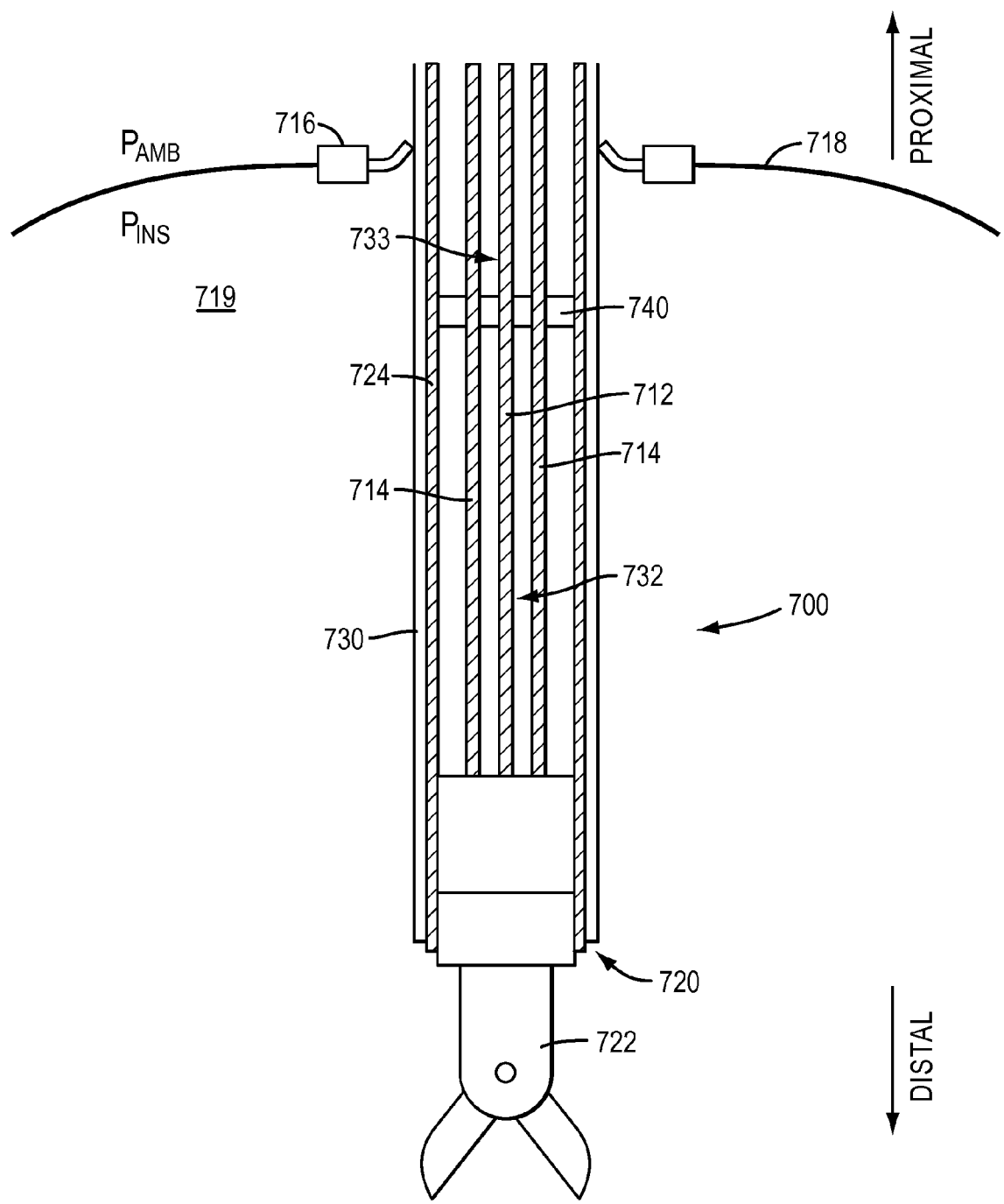
FIG. 7 is a cross-sectional view of an exemplary embodiment of a sheathed surgical instrument including a seal inserted into a body cavity.

According to an exemplary embodiment, a sheathed surgical instrument may be constructed to minimize or prevent the "straw effect" and the consequent introduction of biomaterial into the instrument upon a tear, hole, or other compromise occurring. Turning to FIG. 7, an exemplary embodiment of a sheathed surgical instrument 700 is shown. Sheathed surgical instrument 700 may include, for example, a sheath 730 and an instrument having a proximal end (not shown in the partial view of FIG. 7) and a distal end 720. The proximal and distal directions being labeled as such in FIG. 7. Sheath 730 may have a substantially tubular body, as indicated in FIG. 7, or may include flexible corrugations and other features discussed in the embodiments above. One or more force transmission members 712 (e.g. rod(s) or cable(s)) may extend to the distal end 720 to actuate an end effector 722 and one or more flux conduits or tubes 714 may extend to the distal end 720 to provide electrical power, suction, or another type of flux pathway. The sheathed instrument 700 may be inserted through a body wall 718 of a patient into a body cavity 719, such as through a port 716 located in the body wall 718.

As discussed above, the sheath 730 may be located on an external surface of a shaft 724 of the instrument to serve as a barrier to biomaterial that may otherwise be introduced into the instrument. However, instead of serving as a barrier to separate regions of different pressures, such as the surrounding ambient pressure $P_{AMB}$ from the insufflation pressure $P_{INS}$ within the body cavity 719, sheath 730 may serve to balance the pressure within the instrument with the pressure surrounding the instrument. To do so, sheath 730 may be made of a material that is permeable to gases, such as, for example, insufflation gas. Thus, sheath 730 may permit an equalization of pressure between the pressure within an instrument and the pressure of the environment surrounding the instrument. If a sheath 730 permeable to gas were to be compromised, such as via a puncture or hole through the sheath 730, the "straw effect" may be minimized or prevented because the pressure within the sheathed instrument 700 may be balanced with the pressure external to the sheathed instrument 700. As a result, the introduction of biomaterial via the "straw effect" into a surgical instrument may be minimized or avoided because a pressure differential between the interior of the instrument and the environment surrounding the instrument has been minimized or eliminated.

In addition to being gas-permeable, the material and structure of the sheath 730 may serve as a barrier to liquids and other biomaterial. For instance, the sheath 730 may serve as a barrier or be otherwise impermeable to biomaterials found within a patient's body and liquids used during a surgical procedure. As a result, sheath 730 may serve as a barrier that minimizes or prevents the introduction of biomaterials and other liquids into an instrument but may also be breathable with respect to insufflation gas. Thus, a pressure external to an instrument, such as within a body cavity 719, may be balanced with a pressure within the instrument.

Various materials may be selected to provide a sheath 730 with the properties of acting as a barrier to biomaterials and other liquids while being permeable to gases. According to one exemplary embodiment, a sheath 730 may be made of ePTFE at least along a substantial length of the sheath. Because ePTFE is expanded and porous, it may be permeable to gases that penetrate through the porous structure of ePTFE, while acting as a barrier to liquids, such as blood. According to an exemplary embodiment, sheath 730 may be made of ePTFE having a density ranging from about 0.8 gm/cm$^3$ to about 1.3 gm/cm$^3$. According to an exemplary embodiment, sheath 730 may permit an equalization of pressure between the pressure within an instrument 700 and an insufflation pressure $P_{INS}$ within the body cavity 719 in less than about three seconds. According to another exemplary embodiment, sheath 730 may permit an equalization of pressure between the pressure within an instrument 700 and an insufflation pressure $P_{INS}$ within the body cavity 719 substantially instantaneously. However, the time for equalization of pressure is not limited to these time periods. For instance, the time for equalization of pressure could take longer.

As noted above, a proximal end of a sheathed instrument 700 may be external to a body of a patient and may be exposed to the ambient pressure $P_{AMB}$ of the surrounding environment, such as the environment of an operating room. This may result in the interior of the sheathed instrument being at the ambient pressure $P_{AMB}$, which may be lower than the insufflation pressure $P_{INS}$ within a body cavity 719. Because a sheath 730 may be breathable and permeable to insufflation gas, it may be difficult for the sheath 730 to permit equalization between the pressure within the instrument and the pressure within a body cavity 719. For instance, although a sheath 730 may permit insufflation gas to permeate within the sheathed instrument 700, the insufflation gas is permitted to flow up into the interior of the sheathed instrument 700 (e.g., through openings associated with the end effector, wrist mechanism, etc.) and outside of a patient's body to the surrounding environment, which can prevent an effective equalization of pressure. Further, such an arrangement may interfere with the insufflation of a body cavity 719 because the insufflation gas may be permitted to escape through the sheathed instrument 700, albeit at a relatively slow rate.

To address this, a sheathed instrument 700 may include a seal 740, as shown in the exemplary embodiment of FIG. 7. Seal 740 may be located within an interior of a sheathed instrument 700 to provide an internal seal that fluidically separates a distal end portion 732 of the sheathed instrument 700 from a portion 733 of the sheathed instrument 700 located proximal to seal 740. Thus, seal 740 may substantially prevent gases within the distal portion 732 of the sheathed instrument 700 from passing through and proximally beyond the seal 740, and vice versa. In other words, seal 740 may separate a first pressure within a portion of instrument 700 proximal to seal 740 from a second pressure within a portion of instrument 700 distal to seal 740 so that the second pressure remains substantially greater than the first pressure. As a result, when sheath 730 permits equalization of pressure, the distal portion 732 of the sheathed instrument 700 may be equalized to the insufflation pressure $P_{INS}$ that surrounds the sheathed instrument 700 within the body cavity 719. Thus, the interior of the sheathed instrument 700 within the distal portion 732 may be substantially equalized with the gas at insufflation pressure $P_{INS}$ within the body cavity 719. Conversely, a portion 733 proximal to seal 740 may be sealed from the distal portion 732 so that the portion 733 may remain at ambient pressure $P_{AMB}$.

Seal 740 may include one or more apertures to permit one or more force transmission member(s) 712 and flux conduits 714 to pass through seal 740 to the distal end 720 of the sheathed instrument 700, as shown in the exemplary embodiment of FIG. 7. Seal 740 may form a seal against force transmission member(s) 712 and flux conduits 714, while permitting axial movement of those elements along the long axis of the sheathed instrument 700, such as when a force transmission member 712 is pushed or pulled to actuate the end effector 722. The seal 740 may be located at a position within the sheathed instrument 700 so that when the sheathed instrument 700 is inserted inside a patient's body the seal 740 is located within the body cavity 719, as indicated in FIG. 7, although the position of the seal 740 is not limited in this way. For instance, the seal 740 may be located within the sheathed instrument 700 so that when the sheathed instrument 700 is inserted in the body of a patient the seal 740 is positioned at the body wall 718. In another example, the seal 740 may be positioned proximal to the body wall 718 when the sheathed instrument 700 is inserted within a patient's body.

According to an exemplary embodiment, a sheath 730 may be sealed against the shaft 724 of a surgical instrument. Such a seal may be provided to minimize or prevent leaking of gas along an annular space that otherwise might exist between the sheath 730 and the shaft 724 of the instrument. For instance, when gas, such as insufflation gas, diffuses through sheath 730, the gas could pass between the sheath 730 and the shaft 724 of the instrument if the sheath 730 is not sealed against the shaft 724. Such an arrangement could interfere with the equalization of pressure between the instrument and the pressure within the body cavity 719. To prevent or minimize this, at least a portion of the sheath 730 may be sealed to the instrument shaft 724. For instance, a portion of the sheath 730 located at, or in close proximity to, the seal 740 may be sealed to the instrument shaft 724. In another exemplary embodiment, at least a portion of the sheath 730 may be sealed to the instrument shaft 724 at a location distal from the seal 740. In another example, sheath 730 may be sealed to instrument shaft 724 along the length of the sheath 730. In another example, at least a portion of sheath 730 may be sealed to instrument shaft 724 at a location proximal to seal 740 or along a length of sheath 730 proximal to seal 740.

According to an exemplary embodiment, a sheathed instrument 700 may include both (1) a sheath 730 that is impermeable to liquids and biomaterials but permeable to gas and permits a substantial equalization of pressure between the interior of the sheathed instrument 700 and the surrounding body cavity 719 and (2) a seal 740 to separate the equalized portion of the sheathed instrument 700 from the ambient pressure at the proximal end of the sheathed instrument 700. In other words, providing a sheath 730 that is permeable to gases, such as insufflation gas, and a seal 730 may advantageously permit the sheath 730 to act as a barrier to liquids, such as blood and other liquid biomaterials, while permitting the distal portion 732 of the sheathed instrument 700 to be substantially equalized in pressure with the surrounding body cavity 719 so that if the sheath 730 were to be compromised, a pressure differential between the body cavity 719 and the instrument would be minimized or prevented, which would otherwise cause the "straw effect" that leads to the introduction of biomaterial inside the sheathed instrument 700 and the soiling of the instrument.

FIGS. 8-10 show detailed partial views of exemplary embodiments of surgical instruments. Turning to FIG. 8A, a partial side view of a shaft of a surgical instrument 800 is shown. In the example of FIG. 8A, the surgical instrument 800 does not include a sheath. The surgical instrument 800 may include a distal portion 810 and a proximal portion 820 relative to a seal 850. The distal portion 810 and the proximal portion 820 may be connected or otherwise demarcated by a juncture 830. According to an exemplary embodiment, the distal portion 810 may include one or more holes 840, as shown in FIGS. 8A and 8B. The proximal portion 820 may also include one or more holes 840. Holes 840 may be provided to assist with cleaning of the surgical instrument 800, such as described above for the exemplary embodiment of FIG. 2. In an exemplary embodiment (not shown), the portion 820 proximal to the juncture 830 may not have holes but may be a solid shaft without holes.

According to an exemplary embodiment, juncture 830 may include one or more structures to engage with a sheath. Such structures may engage with a sheath and may function to lock the sheath in a desired location. For instance, juncture 830 may include a first protrusion 832 that engages with a sheath fitted over shaft 812, as shown in the exemplary embodiment of FIG. 8B. First protrusion 832 may generally extend in a direction transverse to a longitudinal axis of shaft 812 and may seal against an inner surface of a sheath. Thus, any annular space that may be present between a sheath and an instrument may be sealed off at juncture 830. Further, protrusion 832 may assist in locking a sheath in place relative to shaft 812. Juncture 830 may include a single protrusion or a plurality of protrusions, such as a further second protrusion 834, as shown in FIG. 8B.

According to the exemplary embodiment shown in FIG. 8B, a seal 850 may be located within the instrument to seal against one or more force transmission member(s) 852 configured to actuate an end effector (not shown) connected to the distal end (not shown) of the shaft 812 and seal against one or more conduits 854 arranged to provide electrical power, signals, suction, water, or other type of flux pathway to the distal end. According to an exemplary embodiment, seal 850 may be made of, for example, silicone or ethylene propylene diene monomer rubber (EPDM rubber). In another exemplary embodiment, seal 850 may include a body that includes an outer coating to minimize friction, such as a coating of silicone, such as a coating of Slick Sil® LSR from Surface Solutions Group of Chicago, Ill. or a coating of Parylene. Further, seal 850 may be a separate component from a sheath and/or an instrument or seal 850 may be over-molded onto a component of an instrument.

As discussed in the embodiments above, a sheath may be formed from a single material or a sheath may be formed from more than one material. For instance, a sheath may be made from multiple materials so that the sheath advantageously benefits from the properties of each material. Turning to FIG. 9A, a side view of an exemplary embodiment of a sheathed surgical instrument 900 is shown. The sheath 902 of the sheathed surgical instrument 900 may include a first sheath portion 940 at a distal portion 910 and a second sheath portion 950 at a proximal portion 920 of the sheathed surgical instrument 900 relative to distal portion 910. The first portion 940 and the second portion 950 of the sheath 902 may be connected at a location that is at the same axial location of an overlap or juncture 930 of shaft 905 when sheath 902 is in position on shaft 905, as will be discussed below.

Although the first sheath portion 940 and the second sheath portion 950 may be formed from the same material in at least one exemplary embodiment, the first sheath portion 940 and the second sheath portion 950 are formed from different materials. For instance, the first sheath portion 940 may be made from one or more materials that are suitable for use at the distal portion 910 of the sheathed surgical instrument 900, which is often flexed and is often inserted into a body cavity environment during use. Further, the second sheath portion 950 may be made from one or more materials that are suitable for use at the proximal portion 920 of the sheathed surgical instrument 900, which may be subjected to more wear than the distal portion 910.

According to an exemplary embodiment, a first sheath portion 940 may be made of ePTFE. As discussed above, ePTFE may provide the first sheath portion 940 at the distal portion 910 of the sheath to be permeable and breathable to gas, such as insufflation gas, which may substantially permit an equalization of pressure between the interior of the sheathed surgical instrument 900 and a surrounding environment inside a body cavity. Further, the ePTFE may serve as a barrier to liquids, such as liquid biomaterials, such as blood. In addition, ePTFE is relatively flexible and will bend with relative ease as the distal portion 910 of the sheathed surgical instrument 900 is bent by a user. For instance, sheathed surgical instrument 900 may include a wrist structure, which an ePTFE sheath would bend with as the wrist structure is actuated.

According to an exemplary embodiment, a second sheath portion 950 may be made of FEP. According to another exemplary embodiment, second sheath portion 950 may be made of a thermoplastic elastomer such as PEBA (e.g., PEBAX®). Although FEP and PEBA might not be as permeable to insufflation gas as ePTFE, FEP and PEBA are more durable than ePTFE. Therefore, it may be advantageous to provide a second sheath portion 950 that is made of FEP or PEBA so that a proximal portion 920 of a sheathed surgical instrument 900 is made of a relatively durable material. Further, according to an exemplary embodiment, a first sheath portion 940 may be made of ePTFE and a second sheath portion 950 may be made of FEP or PEBA so that the sheath may be made of a combination of materials that provide the advantageous properties of ePTFE and FEP or PEBA, particularly at the respective distal portion 910 and proximal portion 920.

According to an exemplary embodiment, a surgical instrument may include one or more features to assist with maintaining a position of a sheath on an instrument shaft. Turning to FIG. 9B, an instrument shaft 905 is shown connected to a sheath, particularly a sheath made of a first sheath portion 940 and a second sheath portion 950. The instrument shaft 905 may include one or more structures that mechanically interact with the sheath to form a seal between an inside surface of a sheath, such as first sheath portion 940 or second sheath portion 950. Further, the structures may assist with maintaining a position of the sheath on the instrument shaft 905 due to friction between the structures and a sheath. As shown in the exemplary embodiment of FIG. 9B, the instrument shaft 905 may include at least one ridge 932 that mechanically interacts or interferes with the sheath. Ridge 932 may be a raised portion of the instrument shaft 905 or an area of greater outer diameter of the instrument shaft 905 so that the ridge 932 presses against an interior surface of the sheath, as shown in FIG. 9B. As a result, the sheath 902 may be force fit against the ridge 932 due to the larger diameter of the ridge 932 in relation to portions of the instrument shaft 905 distal and/or proximal to the ridge 932, which may assist in maintaining the position of the sheath 902. According to an exemplary embodiment, ridge 932 may form a seal with a sheath that may prevent or minimize a flow of gas and/or fluid between the sheath and the instrument shaft 905.

The instrument shaft 905 may include a second ridge 934, as shown in FIG. 9B. Second ridge 934 may be similar to first ridge 932 and may interact with a sheath in the same or a similar manner as first ridge 932 to assist with maintaining the position of the sheath. The first ridge 932 and the second ridge 934 may have the same size, such as the same outer diameter, and the same shape as one another or may differ in size and/or shape. Ridges 932, 934 may be located at overlap portion 930 of the sheath 902, which will be discussed below, or may be located distal or proximal to the overlap 930. Further, although the one or more ridges 932, 934 have been discussed in relation to a sheath made of more than one portion or material, the one or more ridges 932, 934 may be used to assist with connecting a single piece or single material sheath to an instrument.

As shown in FIGS. 9A and 9B, if a sheath includes one or more portions 940, 950, the portions may be connected at an overlap portion 930. According to an exemplary embodiment, one sheath portion may be overlapped with another sheath portion in the overlap portion 930. For instance, as shown in FIG. 9B, an end 942 of first sheath portion 940 may be overlapped with an end 952 of second sheath portion 950. Further, end 942 may be flared outward in a radial direction away from a longitudinal axis of instrument shaft 905 to aid in installation of sheath onto an instrument. For instance, end 942 may be flared outward to minimize or prevent an instrument from catching on end 942 when the sheath is placed on an instrument. In the example of FIG. 9B, end 952 of the second sheath portion 950 is located outside of or external to end 942 of the first sheath portion 940, relative to a central longitudinal axis of the sheathed surgical instrument 900. Such an arrangement may be made, for example, when the first sheath portion 940 is made of ePTFE, which is compliant and may be compressed to form a seal with an instrument, and the second sheath portion 950 is made of FEP or PEBA, which may be more durable than ePTFE and are stiffer than ePTFE so that the second sheath portion 950 may be stiffer and more rigid than the first sheath portion 940. Thus, the second sheath portion 950 may facilitate compression of the first sheath portion 940 against an instrument to form a seal with the instrument. These positions may be reversed, with first sheath portion 940 being located on top of, or external to, the second sheath portion 950.

According to an exemplary embodiment, a joint portion 530 of a sheath may include a bond between a first sheath portion 940 and a second sheath portion 950. For instance, a first sheath portion 940 and a second sheath portion 950 may be thermally bonded to one another, adhesively bonded, mechanically fastened together, or joined by other methods used in the art to form a seal between first sheath portion 940 and second sheath portion 950. Such bonds may be used in combination with one another and may be used in combination with the overlapping arrangement discussed above and shown in the exemplary embodiment of FIG. 9B. For instance, a first sheath portion 940 and a second sheath portion 950 may be overlapped with one another and further joined together by a thermal bond.

According to an exemplary embodiment, when a sheath includes one or more portions 940, 950, the sheath portions 940, 950 may be joined together at overlap or joint portion 930, as discussed above, and the sheath may be held in position on an instrument shaft 905, such as via a friction fit with one or more ridges 932, 934. As a result, a double seal may be formed, with the sheath portions 940, 950 sealed together and the sheath contacting the instrument shaft 905, such as via one or more ridges 932, 934, to seal an annular space that may otherwise be formed between the sheath and the instrument shaft 905.

Turning to FIG. 10A, a side view of a sheathed surgical instrument 1000 is shown. Sheathed surgical instrument 1000 may include the features discussed in FIGS. 8A, 8B, 9A, 9B. For instance, a sheath 1002 of the sheathed surgical instrument 1000 may be made of more than one material, with a first sheath portion 1040 at a distal portion 1010 of instrument and a second sheath portion 1050 at a proximal portion 1020 relative to distal portion 1010. The first sheath portion 1040 and the second sheath portion 1050 may be joined at an overlap or joint portion 1030. Further, as shown in FIG. 10B, an end 1042 of the first sheath portion 1040 and an end 1052 of the second sheath portion 1050 may be joined and/or overlapped with one another, as discussed above. As described above, a seal 1060 may be located within an instrument shaft 1005 to seal against one or more force transmission member(s) 1062 and seal against one or more flux conduits or tubes 1064. The sheathed surgical instrument 1000 may further include one or more ridges (not shown) to seal the sheath to an instrument shaft 1005, as discussed with regard to the exemplary embodiment of FIG. 9B.

According to an exemplary embodiment, a distal end of a sheath may be fitted to a surgical instrument. Turning to FIGS. 11A and 11B, a partial view of a distal portion of a sheathed surgical instrument 1100 is shown that includes a sheath 1110, an end effector 1120 of a surgical instrument extending through the sheath 1110, and a retaining cuff 1112 where the sheath 1110 may be joined to the surgical instrument. According to an exemplary embodiment, retaining cuff 1112 may be made of a heat shrinkable material, such as PTFE or FEP, or a material capable of a thermal bond, such as PEBA or FEP. Sheath 1110 may be joined to the surgical instrument by, for example, a thermal bond. For instance, sheath 1110 may be heat shrunk to the surgical instrument. In another instance, retaining cuff 1112 may be made of a material that may be heat shrunk so that its inner diameter is reduced and retaining cuff 1112 presses sheath 1110 against the shaft of a surgical instrument. In another instance, both sheath 1110 and retaining cuff 1112 may be heat shrunk to a surgical instrument. Further, a surgical instrument may include one or more protrusions 1114 that serve as distal shoulders to engage with sheath 1110 to lock sheath in place and/or to form a seal with sheath 1110.

The manner of joining the sheath 1110 to the surgical instrument, however, is not limited to thermal bonding. For instance, the sheath 1110 may be joined to the surgical instrument by a radial compression, such as by arranging retaining cuff 1112 to press sheath 1110 against the shaft of a surgical instrument. For example, retaining cuff may be arranged similarly to end piece 330 discussed above in regard to FIG. 3C to tightened around an exterior surface of the sheath 1110 and press the sheath 1110 against the surgical instrument, or by other joining methods used in the art. Further, as discussed above, an instrument may include one or more protrusions 1114 to engage with sheath 1110 to lock sheath in place and/or to form a seal with sheath 1110.

As mentioned above, another consideration when using a surgical instrument is whether there are any exposed portions of the instrument. Besides a chance of becoming exposed to biomaterials and other substances that may soil the surgical instrument, exposed portions of the instrument may permit contact with one or more moving parts of a surgical instrument. Exposed moving parts could engage tissue, which may become caught upon the moving parts.

Figure 12:
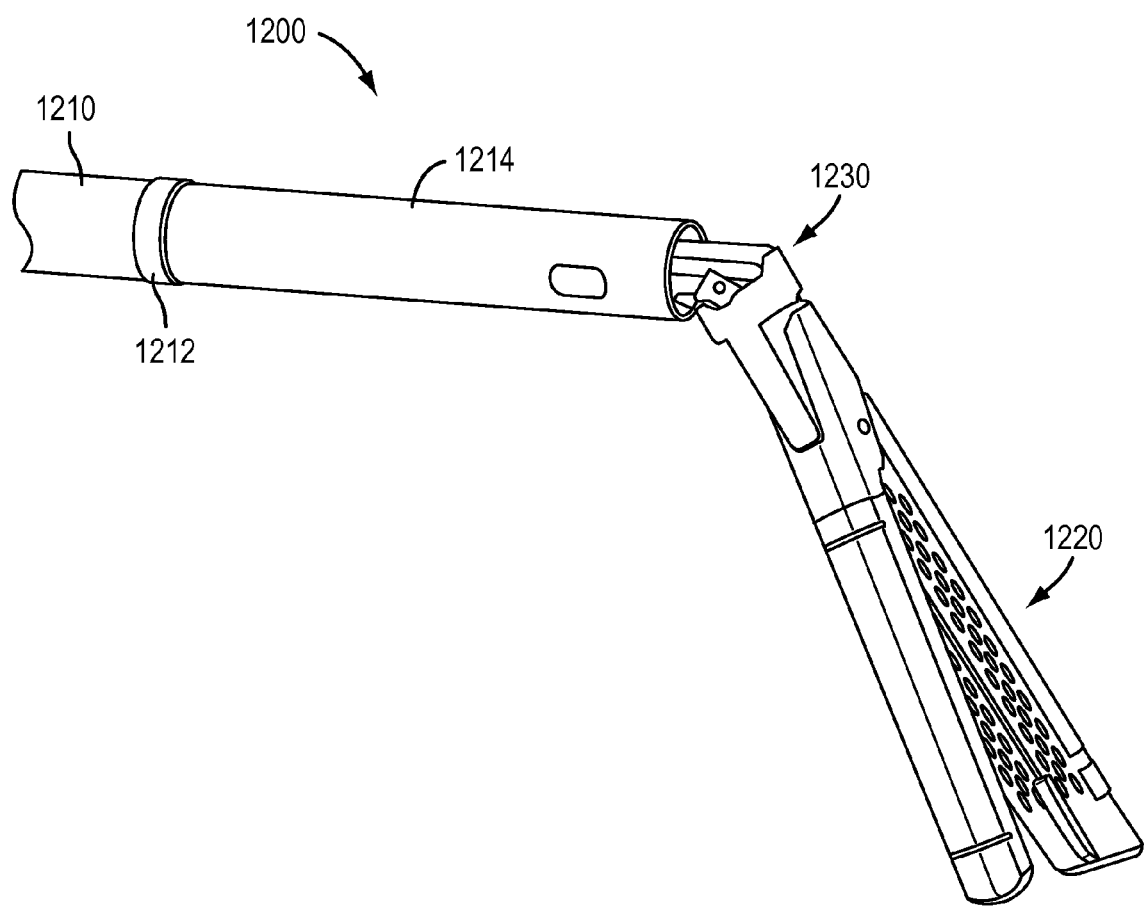
FIG. 12 is a perspective view of another exemplary embodiment of a surgical instrument.

Turning to FIG. 12, an exemplary embodiment of a surgical instrument 1200 is shown. Surgical instrument 1200 may include a shaft 1210 and an end effector 1220. End effector 1220 may be a stapler, as indicated in the exemplary embodiment of FIG. 12, or may be another type of end effector used in a surgical instrument. End effector 1220 may be connected to the shaft 1210 by a wrist 1230 or other type of joint or connection, as shown in the exemplary embodiment of FIG. 12. Wrist 1230 may include moving parts or other structures that may be exposed to tissues and other biomaterials within a body, which may result in tissue becoming caught upon the wrist 1230.

Figure 13:
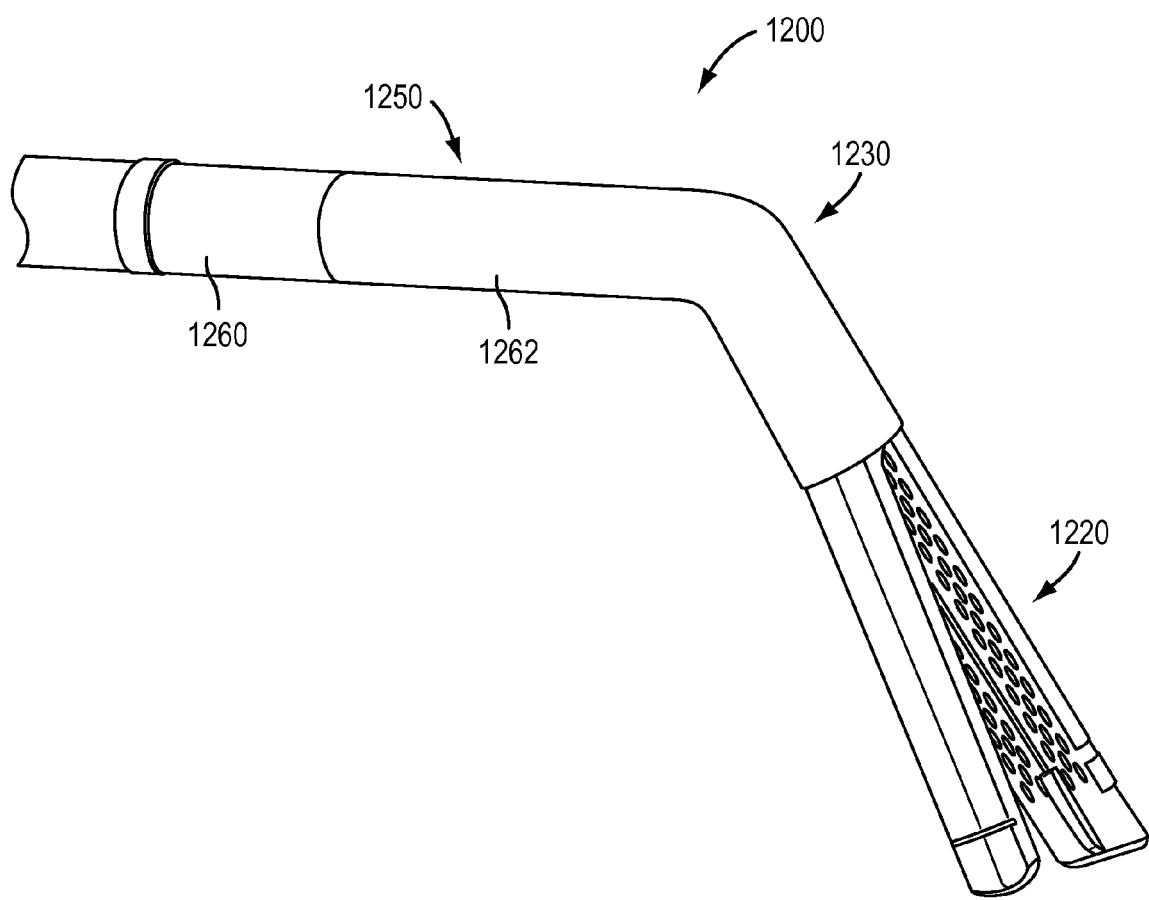
FIG. 13 is a perspective view of the surgical instrument of FIG. 12 with a sheath.

Turning to FIG. 13, an exemplary embodiment of instrument 1200 is shown with a sheath 1250. As shown in FIG. 13, sheath 1250 may extend over wrist 1230. Thus, sheath 1250 may serve as a protective barrier that covers the wrist so that the parts and structures of wrist 1230 may be covered and not exposed. According to an exemplary embodiment, sheath 1250 may extend up to the end effector 1220, as shown in FIG. 13. This positioning may enable sufficient coverage over parts that could be more prone to entry of biomaterials and also tangling with other instruments and/or parts of a patient without hindering movement and operation of the end effector 1220.

As discussed above, sheath 1250 may include one or more materials. For instance, sheath 1250 may include a first sheath portion 1260 made of a first material and a second sheath portion 1262 made of a second material. According to an exemplary embodiment, the second material of the second sheath portion 1262 may be a relatively flexible material. Further, the second material may be a material that is permeable to gases, such as insufflation gas, and may substantially permit an equalization of pressure to minimize or prevent the "straw effect" discussed above. For instance, the second material of the second sheath portion 1262 may be ePTFE. According to an exemplary embodiment, the first material of the first sheath portion 1260 may be a relatively durable material because, for example, first sheath portion 1260 is located over wrist 1230 and subjected to forces when wrist 1230 is actuated and when the instrument is inserted into a patient. For instance, the first material of the first sheath portion 1260 may be FEP.

Instrument 1200 may include one or more structures to connect sheath 1250 to the instrument 1200. According to an exemplary embodiment, instrument 1200 may include the ridges discussed in regard to the embodiment of FIG. 9B. For instance, instrument 1200 may include a first ridge 1212 and a second ridge 1214, as shown in the exemplary embodiment of FIG. 12. First ridge 1212 and second ridge 1214 may be spaced apart a distance corresponding to a length of the first sheath portion 1260 so that the ridges 1212, 1214 are located at the proximal and distal ends of the first sheath portion 1260. As a result, ridges 1212, 1214 may advantageously serve to hold first sheath portion 1260 in place relative to instrument 1200. Instrument 1200 may include other features to maintain a position of sheath 1250 on the instrument, such as the distal retention features discussed in regard to the embodiment of FIGS. 11A and 11B.

Figure 14A:
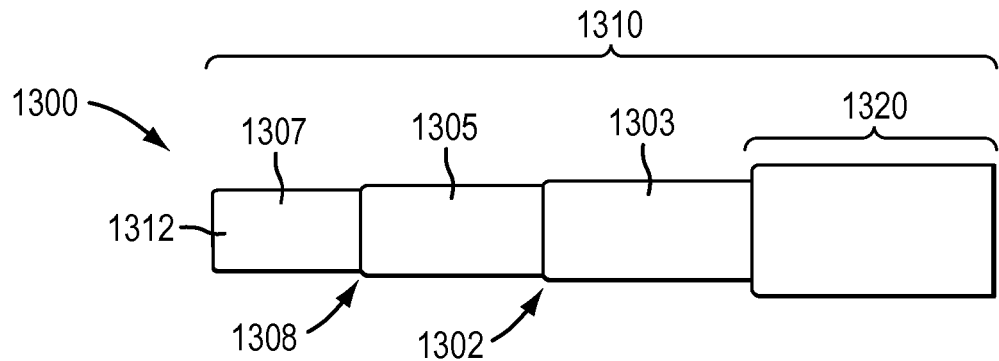
FIG. 14A is a side view of another exemplary embodiment of a sheathed surgical instrument.
Figure 14B:
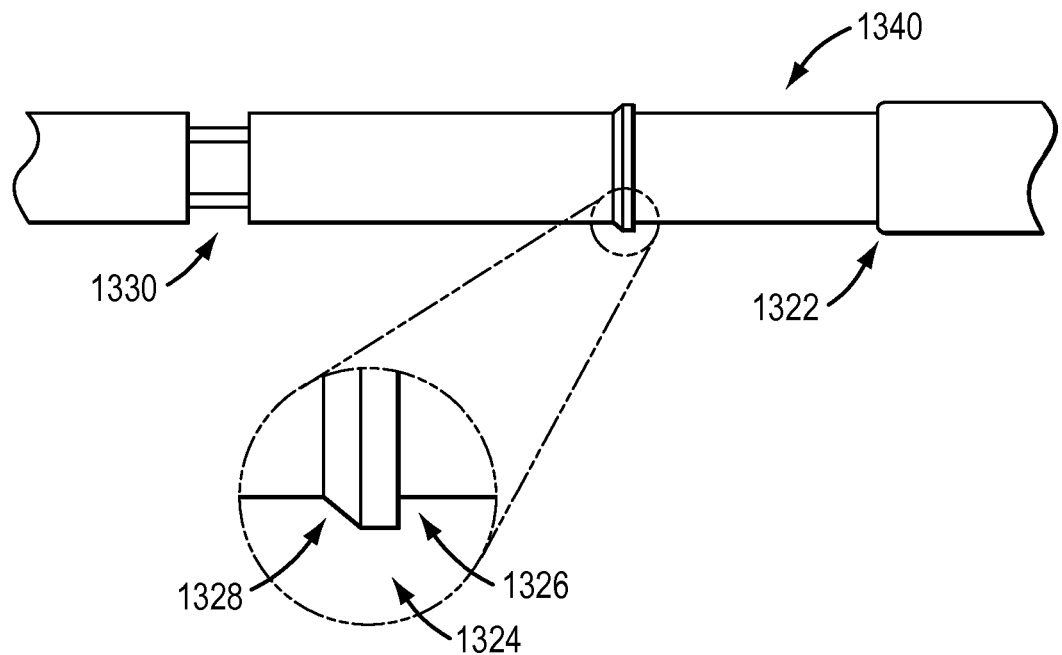
FIG. 14B is a side view of the surgical instrument of FIG. 14A with the sheath removed.

Turning to FIG. 14A, an exemplary embodiment of a sheathed surgical instrument 1300 is shown. As discussed in the embodiments above, the sheath may be made from one or more materials. For instance, a first portion 1310 of sheath may be made of a first material, such as ePTFE, and a second portion 1320 of sheath may be made of a second material, such as FEP. In other embodiments, second portion 1320 of sheath may be made of PEBA. To secure the position of the second sheath portion 1320, an instrument 1340 may include a shoulder 1322 and a snare 1324, as shown in FIG. 14B. Snare 1324 may include a ridge 1326 that is spaced apart from shoulder 1322 a distance corresponding to a length of second sheath portion 1320 so that the second sheath portion 1320 may be constrained between shoulder 1322 and the ridge 1326 of the snare 1324. First sheath portion 1310 may extend over a distal portion of the instrument 1340. The distal portion of instrument 1340 covered by first sheath portion 1310 may include a wrist portion 1330, as shown in FIG. 14B, or instrument 1340 may lack a wrist portion 1330. To assist with securing the first sheath portion 1310 to the instrument 1340, snare 1324 may include a sloped portion 1328 so that first sheath portion 1310 may be stretched over the sloped portion 1328. Conversely, a distal end 1312 of the first sheath portion 1310 may not be connected to the instrument 1340, permitting the distal end 1312 of the sheath to move relative to instrument 1340.

According to an exemplary embodiment, instrument 1340 may be tapered to assist with fitting a sheath to be fit over the instrument 1340 while permitting the sheath to still be slid onto the instrument. For instance, as shown in the exemplary embodiment of FIG. 14A, an instrument may have a first section 1303 having a greater diameter than a second section 1305, with the second section 1305 having a greater diameter than a third section 1307. First section 1303 may have diameter of approximately 0.48 inches to approximately 0.52 inches, second section 1305 may have diameter of approximately 0.46 inches to approximately 0.48 inches, and third section 1307 may have diameter of approximately 0.44 inches to approximately 0.46 inches.

Figure 5:
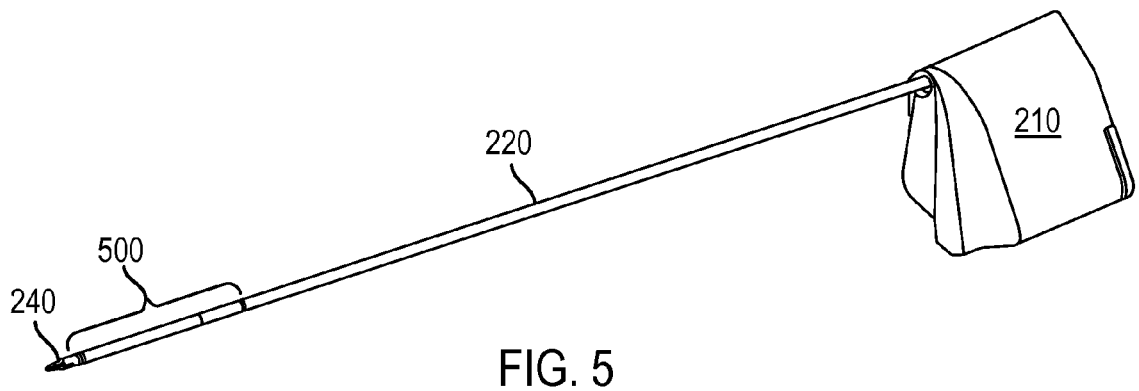
FIG. 5 illustrates an instrument in accordance with an exemplary embodiment in which a replaceable sheath covers a wrist mechanism of the instrument but does not extend the length of the main tube of the instrument.

Sheaths as described above can cover all or most of the length of main shaft 220 and wrist mechanism 230 of an instrument 200 and particularly cover portions of the instrument that require electrical isolation, a barrier to biological material and liquids, or sealing to prevent loss of cavity pressure during a medical procedure. However, in an alternative embodiment of the invention, a replaceable sheath can be of more limited length and designed primarily to cover and seal a wrist mechanism or joint. FIG. 5, for example, shows an instrument having a replaceable sheath 500 that extends from end effector 240 to the distal end of main shaft 220, thereby covering and sealing the wrist mechanism of the instrument. The portion of main shaft 220 not covered by sheath 500 can be left bare if sealing or electrical isolation of main shaft 220 is not required or can be covered by a permanent coating or sheath that is not easily removable or replaceable.

A sheath covering a wrist mechanism, whether or not the remainder of the main tube of an instrument is covered, can be used to apply lubricants or agents to the wrist mechanism or other components of the instrument. For example, a medically safe lubricant such as mineral oil or Aesculap Sterilit oil can be coated on the interior of a sheath so as to come in contact with the wrist mechanism of an instrument when the removable sheath is installed on the instrument. In such a case, installation of the sheath and operation of the wrist mechanism can cause the lubricant to work into the wrist mechanism, resulting in less operating friction and less wear on mechanical joints. Alternatively or additionally, an agent that facilitates cleaning of an instrument can similarly be provided within the interior of the sheath. For example, an anticoagulant such as Heparin could be provided within a sheath so that biological material that somehow reaches the interior of the instrument is less likely to stick to the instrument and is more easily cleaned out of the instrument. Alternatively, the agent could be a disinfectant.

By providing a sheath that is permeable to gases, such as insufflation gas, the interior pressure of a sheathed instrument may be substantially equalized with the pressure of a surrounding environment, which may advantageously minimize or prevent the introduction of biomaterial into the instrument. As a result, contamination of the instrument may be reducing and less cleaning of the instrument may be required. Further, a sheathed instrument may be provided that includes a permeable sheath and a seal to separate a proximal end of the instrument, which may be exposed to a surrounding atmospheric pressure, from a distal end of the instrument, which may be substantially equalized with an environment having a pressure greater than the pressure of the ambient environment.

Further modifications and alternative embodiments will be apparent to those of ordinary skill in the art in view of the disclosure herein. For example, the systems and the methods may include additional components or steps that were omitted from the diagrams and description for clarity of operation. Accordingly, this description is to be construed as illustrative only and is for the purpose of teaching those skilled in the art the general manner of carrying out the present teachings. It is to be understood that the various embodiments shown and described herein are to be taken as exemplary. Elements and materials, and arrangements of those elements and materials, may be substituted for those illustrated and described herein, parts and processes may be reversed, and certain features of the present teachings may be utilized independently, all as would be apparent to one skilled in the art after having the benefit of the description herein. Changes may be made in the elements described herein without departing from the spirit and scope of the present teachings and following claims.

It is to be understood that the particular examples and embodiments set forth herein are non-limiting, and modifications to structure, dimensions, materials, and methodologies may be made without departing from the scope of the present teachings.

Other embodiments in accordance with the present disclosure will be apparent to those skilled in the art from consideration of the specification and practice of the invention disclosed herein. It is intended that the specification and examples be considered as exemplary only, with a true scope and spirit being indicated by the following claims.

What is claimed is:

1. A surgical apparatus, comprising:
    a shaft having a proximal end, a distal end, and a lumen extending between the proximal end and the distal end, wherein a portion of the shaft including the distal end is configured to be inserted into an environment at a surgical insufflation gas pressure;
    an end effector coupled to the distal end of the shaft;
    an internal seal disposed within the lumen at a position along the portion of the shaft, wherein the internal seal fluidically separates a first portion of the lumen distal to the internal seal from a second portion of the lumen proximal to the internal seal, wherein the second portion of the lumen is at a pressure lower than the surgical insufflation gas pressure in an inserted position of the portion of the shaft into the environment; and
    a sheath disposed around an external surface of at least the portion of the shaft;
    wherein the sheath comprises a material that is permeable to gas; and
    wherein, in the inserted position of the portion of the shaft into the environment, the internal seal and the sheath are configured to equalize a pressure in the first portion of the lumen to approximately the surgical insufflation gas pressure.

2. The surgical apparatus of claim 1, wherein the material of the sheath that is permeable to gas is impermeable to biomaterial liquids.

3. The surgical apparatus of claim 1, wherein the sheath is configured to seal against the external surface of at least the portion of the shaft.

4. The surgical apparatus of claim 3, wherein the sheath is configured to seal against the external surface of at least the portion of the shaft at a location proximate the distal end of the shaft.

5. The surgical instrument of claim 1, wherein the internal seal includes at least one aperture, wherein a rod or cable arranged to actuate an end effector of the instrument passes through the aperture, and wherein the internal seal seals against the rod or cable.

6. The surgical apparatus of claim 5, wherein the internal seal extends across an entirety of a width of the lumen to seal against an internal wall of the shaft that forms the lumen.

7. The surgical apparatus of claim 1, wherein the sheath comprises ePTFE.

8. The surgical apparatus of claim 1, wherein a first portion of the sheath is made of ePTFE and a second portion of the sheath is made of PEBA.

9. The surgical apparatus of claim 1, wherein a first portion of the sheath is made of ePTFE and a second portion of the sheath is made of FEP.

10. The surgical apparatus of claim 9, wherein the first portion of the sheath and the second portion of the sheath are joined to one another.

11. The surgical apparatus of claim 10, further comprising a retaining cuff connecting the first portion of the sheath to the distal end of the shaft.

12. The surgical apparatus of claim 10, further comprising one or more protrusions at the distal end of the shaft that engage the first portion of the sheath.

13. The surgical apparatus of claim 9, wherein the first portion of the sheath and the second portion of the sheath overlap at a joint portion of the sheath.

14. The surgical apparatus of claim 9, wherein the shaft includes a ridge configured to engage with the sheath and assist in maintaining the sheath in position around the external surface of at least the portion of the sheath.

15. The surgical apparatus of claim 14, wherein the ridge is located at the joint portion of the sheath.

16. The surgical apparatus of claim 14, wherein the shaft further includes a shoulder distal to the ridge, and wherein the ridge and the shoulder are spaced apart at a distance corresponding to a length of the second portion of the sheath and are configured to constrain the second portion of the sheath between the ridge and the shoulder.

17. The surgical apparatus of claim 1, wherein at least the portion of the shaft includes a plurality of holes leading to an interior of the shaft.

18. The surgical apparatus of claim 1, wherein the apparatus is a surgical instrument for a teleoperated surgical system.

19. The surgical apparatus of claim 1, wherein the end effector is coupled to the distal end of the shaft via a wrist structure, and wherein the sheath covers the wrist structure.

20. The surgical apparatus of claim 1, wherein the sheath has a density in a range of about 0.8 gm/cm$^3$ to about 1.3 gm/cm$^3$.

21. The surgical apparatus of claim 1, wherein the material of the sheath that is permeable to gas is permeable to carbon dioxide, and wherein the sheath permits the equalization of pressure in less than three seconds.

22. A surgical apparatus, comprising:
a shaft having a proximal end and a distal end;
an end effector coupled to the distal end of the shaft; and
a sheath disposed around an external surface of the instrument shaft;
wherein the sheath comprises a material that is permeable to gas so as to permit equalization of a pressure differential after insertion of the sheath and shaft into an environment at a surgical insufflation gas pressure;
wherein the pressure differential is between an insufflation gas pressure and an initial pressure lower than the insufflation gas pressure;
wherein a first portion of the sheath is made of ePTFE and a second portion of the sheath is made of FEP; and
wherein the first portion of the sheath is located proximate to a distal end of the shaft and the second portion of the sheath is located proximal to the first portion of the sheath.

23. The surgical apparatus of claim 22, wherein the second portion is a retaining cuff disposed at a proximal end of the sheath.

* * * * *